United States Patent [19]

Blizzard et al.

[11] Patent Number: 4,978,656
[45] Date of Patent: Dec. 18, 1990

[54] SYNTHETIC DERIVATIVES OF PARAHERQUAMIDE

[75] Inventors: Timothy A. Blizzard, Rahway; Helmut Mrozik, Matawan; Gaye Marino, North Bergen, all of N.J.; Peter J. Sinclair, Suffern, N.Y.

[73] Assignee: Merck & Co., Inc., Rahway, N.J.

[21] Appl. No.: 231,318

[22] Filed: Aug. 12, 1988

[51] Int. Cl.$^5$ .................. C07D 491/22; A61K 31/495
[52] U.S. Cl. ........................................ 514/63; 514/81; 514/250; 544/229; 544/230
[58] Field of Search ................ 544/230, 229; 514/250, 514/81, 63

[56] References Cited

U.S. PATENT DOCUMENTS 4,873,247 10/1989 Goegelman et al. ................ 544/230
4,923,867 5/1990 Blizzard et al. ..................... 544/230

OTHER PUBLICATIONS

Yamazaki et al., Chemical Abstracts, vol. 95, No. 19321 (1981).
Yamazaki et al. *Tetrahedron Letter* 22 pg. 135–136 (1981).

*Primary Examiner*—Mukund J. Shah
*Assistant Examiner*—E. Bernhardt
*Attorney, Agent, or Firm*—Hesna J. Pfeiffer; David L. Rose

[57] ABSTRACT

There are disclosed synthetic derivatives of the natural product paraherquamide. The synthetic derivatives are prepared by reactions at the parahequamide A, B, E, F and G rings, that is at carbon atoms 14 to 16, the lactam ring and carbon atoms 24 to 26 as well as carbon atoms 5 and 12. The compounds are active antiparasitic agents and compositions for that use are also disclosed.

26 Claims, No Drawings

SYNTHETIC DERIVATIVES OF PARAHERQUAMIDE

BACKGROUND OF THE INVENTION

Paraherquamide is a known compound disclosed in Yamazaki et al *Tetrahedron Letters* 22 135 136 (1981). No utility for the compounds is disclosed for paraherquamide and the 24,25 dihydro derivative thereof, also disclosed in Yamazaki et al.

Paraherquamide has the following structures:

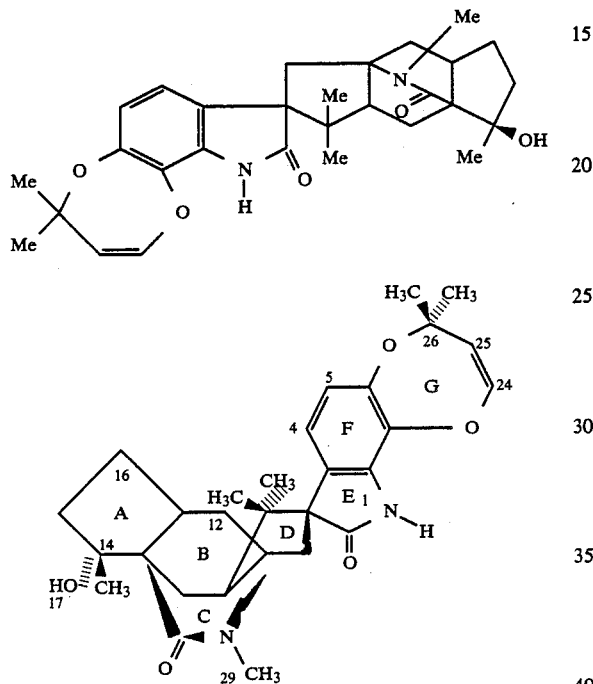

The first structure is the form used by Yamazaki et al. The second structure is the form used herein and is preferred for clarity and the better display of stereochemistry.

Paraherquamide is prepared by the culturing of a fungus *Penicillium parahequi* as described in Yamazaki et al which also discloses the preparation of the 24,25-dihydro derivatives. Paraherquamide is also prepared by the culturing of the fungus *Penicillium charlesi* as described herein.

SUMMARY OF THE INVENTION

Paraherquamide is a known compound which is reacted at numerous positions around the paraharquamide molecule to prepare derivatives thereof with significant antiparasitic and anthelmintic activity. Thus, it is an object of this invention to describe such paraherquamide derivatives. It is a further object to describe processed for the preparation of such derivatives. A still further object is to describe the treatment of parasitic and helmintic infections using the novel compounds of this invention. A still further object is to describe compositions containing the novel compounds as the active ingredient thereof for the treatment of parasitic infections. Further objects will be apparent from a reading of the following description.

DESCRIPTION OF THE INVENTION

The compounds of the instant invention are best realized in the following structure:

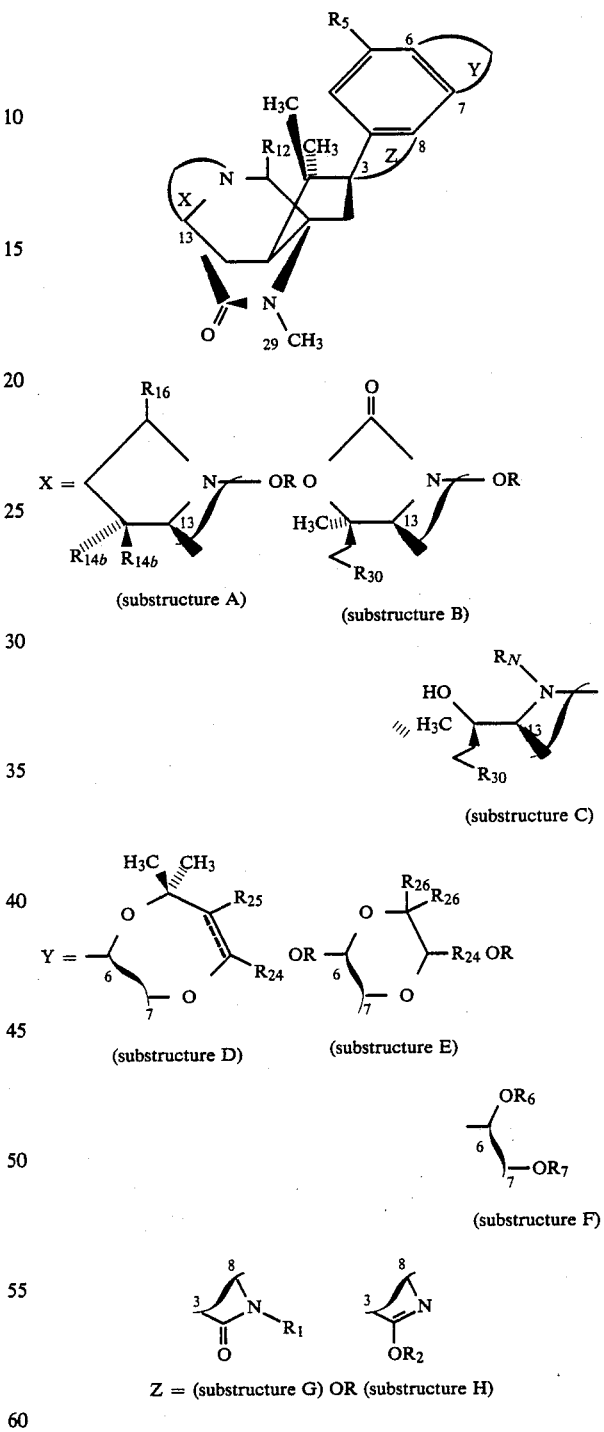

$Z$ = (substructure G) OR (substructure H)

wherein:

$R_1$ is hydrogen, loweralkyl, lower alkanoyl, or substituted benzenesulfonyl;

$R_2$ is loweralkyl;

$R_5$ is hydrogen, halogen, amino, nitro, or loweralkanoylamino;

$R_6$ is hydrogen, loweralkyl, or lower alkanoyl;

$R_7$ is hydrogen, loweralkyl, or lower alkanoyl;

$R_{12}$ is hydrogen or $R_{12}$ can be ketone provided that $R_{16}$ is hydrogen;

$R_{14a}$ is hydrogen, hydroxy, lower alkoxy, lower alkenylloweralkyloxy, lower alkynylloweralkyl oxy, lower alkanoyloxy, polyalkoxyalkyloxy, phenyl, lower alkyl, triloweralkylsilyloxy, diphenylphosphoryloxy, or halogen;

$R_{14b}$ is hydrogen, hydroxy, lower alkyl, lower alkenyl, phenyl, phenylloweralkyl, lower alkoxy, or lower alkanoyloxy,;

$R_{16}$ is hydrogen or $R_{16}$ can be detone provided that $R_{12}$ is hydrogen;

$R_{24}$ is hydrogen, halogen, hydroxy, loweralkoxy, loweralkanoyloxy, or triloweralkylsilyloxy;

$R_{25}$ is hydrogen or halogen;

$R_{26}$ is hydrogen or methyl;

$R_{30}$ is hydrogen, halogen, hydroxy, loweralkoxy, loweralkanoyloxy, hydrazone, or semicarbazone;

$R_N$ is hydrogen or loweralkyl; and the broken line represents a single or double bond between carbons 24 and 25;

provided that the various R groups are not such that the compounds paraherquamide, 24,25 dihydroparaherquamide, 14-deoxyparaherquamide, and 14-deoxy-14-demethyl paraherquamide are defined.

In the instant invention, the term "lower alkyl" is intended to include those alkyl groups of from 1 to 6 carbon atoms in either a straight or branched chain. Examples of such lower alkyl group are methyl, ethyl, propyl, isopropyl, butyl, sec-butyl, pentyl, hexyl and the like.

The term "loweralkenyl" is intended to include those alkenyl groups of from 2 to 6 carbon atoms of either a straight or branched chain with from 1 to 3 double bonds. Examples of such loweralkenyl groups are ethenyl, propenyl, butenyl, 1,3 butedienyl, pentenyl, hexenyl and the like.

The term "loweralkynyl" is intended to include those alkynyl groups of from 2 to 6 carbon atoms of either a straight or branched chain with one triple bond. Examples of such loweralkynyl groups are ethynyl, propynyl, butynyl, pentynyl, hexynyl and the like.

The term "lower alkoxy" is intended to include those alkoxy groups of from 1 to 6 carbon atoms in either a straight or branched chain. Examples of such lower alkoxy group are methoxy, ethoxy, propoxy, isopropoxy, n-butoxy, sec-butoxy, tert-butoxy, pentoxy, hexoxy and the like.

The term "lower alkanoyl" is intended to include those alkanoyl groups of from 2 to 6 carbon atoms in either a straight or branched chain. Examples of such lower alkanoyl group are acetyl, propionyl, isopropionyl, butyryl, pentanoyl, hexanoyl and the like.

The term "halogen" is intended to include the halogen atoms fluorine, chlorine, bromine, and iodine.

The term "substituted benzenesulfonyl" is defined as mono, di, or tri-alkyl-benzenesulfonyl, mono, di, or tri-alkoxy-benzenesulfonyl, or mono, di, or tri-halo-benzenesulfonyl.

The term "poly alkoxyalkoxy" is defined as from 2 to 4 loweralkoxy groups of either a linear or branched carbon chain in a linear arrangement of alkoxy groups. Examples of such polyalkoxy alkoxy groups are methoxyethoxy, ethoxy ethoxy, methoxyethoxy methoxy, methoxyethoxy ethoxy, methoxy methoxyethoxy ethoxy, and the like.

Preferred compounds of this invention are realized when:

$R_1$ is hydrogen, loweralkyl, lower alkanoyl, or substituted benzenesulfonyl;

$R_2$ is loweralkyl;

$R_5$ is hydrogen, halogen, amino, nitro, or loweralkanoylamino;

$R_6$ is hydrogen, loweralkyl, or lower alkanoyl;

$R_7$ is hydrogen, loweralkyl, or lower alkanoyl;

$R_{12}$ is hydrogen or $R_{12}$ can be ketone provided that $R_{16}$ is hydrogen;

$R_{14a}$ is hydrogen, hydroxy, lower alkoxy, lower alkenylloweralkyloxy, lower alkynylloweraIlkyloxy, lower alkanoyloxy, polyalkoxyalkyloxy, phenyl, lower alkyl, trialkysilyloxy, diphenylphosphoryloxy, or halogen;

$R_{14b}$ is hydrogen, hydroxy, lower alkyl, lower alkenyl, phenyl, phenylloweralkyl, lower alkoxy, or lower alkanoyloxy,;

$R_{16}$ is hydrogen or $R_{16}$ can be ketone provided that $R_{12}$ is hydrogen;

$R_{24}$ is hydrogen, halogen, hydroxy, loweralkoxy, loweralkanoyloxy, or trialkylsilyloxy;

$R_{25}$ is hydrogen or halogen;

$R_{26}$ is hydrogen or methyl;

$R_{30}$ is hydrogen, halogen, hydroxy, loweralkoxy, loweralkanoyloxy, hydrazone, or semicarbazone;

$R_N$ is hydrogen or loweralkyl; and the broken line represents a single or double bond between carbons 24 and 25;

provided that the various R groups are not such that the compounds paraherquamide, 24,25-dihydroparaherquamide, 14-deoxyparaherquamide, and 14-deoxy-14-demethyl paraherquamide are defined.

More preferred compounds of this invention are compounds wherein:

X is substructure B

Y is substructure D

Z is substructure G $R_1$ is hydrogen, lower alkyl, lower alkanoyl, or substituted benzenesulfonyl $R_5$ is hydrogen, halogen, amino, nitro, or lower alkanoylamino;

$R_{24}$ is hydrogen, halogen, hydroxy, loweralkoxy, loweralkanoyloxy, or triloweralkylsilyloxy;

$R_{25}$ is hydrogen or halogen;

$R_{30}$ is hydrogen, halogen, hydroxy, loweralkoxy, loweralkanoyloxy, hydrazone, or semicarbazone; and The broken line represents a single or double bond between carbons 24 and 25.

Still more preferred compounds of this invention are realized when:

$R_1$ is hydrogen or substituted benzenesulfonyl;

$R_5$ is hydrogen, $R_{24}$ is hydrogen or loweralkoxy;

$R_{25}$ is hydrogen;

$R_{30}$ is hydrogen, halogen, hydroxy, loweralkoxy, loweralkanoyloxy, hydraxone, or semicarbazone; and the broken line represents a single or double bond between carbons 24 and 25.

Additional preferred compounds of this invention are realized when:

X is substructure A

Y is substructure E

Z is substructure G $R_1$ is hydrogen, loweralkyl, lower alkanoyl, or substituted benzenesulfonyl;

$R_5$ hydrogen, halogen, amino, nitro, or loweralkanoylamino;

$R_{12}$ is hydrogen or $R_{12}$ can be ketone provided that $R_{16}$ is hydrogen;

$R_{14a}$ is hydrogen, hydroxy, lower alkoxy, lower alkenylloweralkyloxy, lower alkynylloweralkyloxy, lower alkanoyloxy, polyalkoxyalkyloxy, phenyl, lower alkyl, triloweralkylsilyloxy, diphenylphosphryloxy, or halogen;

$R_{14b}$ hydrogen, hydroxy, lower alkyl, lower alkenyl, phenyl, phenylloweralkyl, lower alkoxy, or lower alkanoyloxy,;

$R_{16}$ is hydrogen or $R_{16}$ can be ketone provided that $R_{12}$ is hydrogen;

$R_{24}$ is hydrogen, halogen, hydroxy, loweralkoxy, loweralkanoyloxy, or trialkylsilyloxy;

$R_{26}$ is hydrogen or methyl:

More preferred compounds of this invention are realized when:

$R_1$ is hydrogen or substituted benzenesulfonyl;

$R_5$ is hydrogen $R_{12}$ is hydrogen $R_{14a}$ is hydrogen, hydroxy, lower alkoxy, lower alkenylloweralkyloxy, lower alkynylloweralkyloxy, lower alkanoyloxy, polyalkoxyalkyloxy, or triloweralkylsilyloxy;

$R_{14b}$ is hydrogen, lower alkyl, lower alkenyl, phenyl, or phenylloweralkyl;

$R_{16}$ is hydrogen;

$R_{24}$ is hydrogen, halogen, hydroxy, loweralkoxy, loweralkanoyloxy, or triloweralkylsilyloxy;

$R_{26}$ is hydrogen or methyl.

Still more preferred compounds of this invention are realized when:

$R_1$ is hydrogen;

$R_5$ is hydrogen $R_{12}$ is hydrogen $R_{14a}$ is hydroxy, lower alkoxy, lower alkenylloweralkyloxy, or lower alkynylloweralkyloxy;

$R_{14b}$ is hydrogen, lower alkyl, or lower alkenyl;

$R_{16}$ is hydrogen;

$R_{24}$ hydrogen, halogen, hydroxy, or loweralkoxy;

$R_{26}$ is hydrogen or methyl.

Additional preferred compounds of this invention are realized when:

X is structure A

Y is substructure D

Z is substructure G $R_1$ is hydrogen, lower alkanoyl, or substituted bezenesulfonyl;

$R_5$ is hydrogen, halogen, amino, nitro, or loweralkanoylamino;

$R_{12}$ is hydrogen;

$R_{14a}$ is hydrogen, hydroxy, lower alkoxy, lower alkenylloweralkyloxy, lower alkynylloweralkyloxy, lower alkanoyloxy, polyalkoxyalkyloxy, phenyl, lower alkyl, triloweralkylsilyloxy, diphenylphosphoryloxy, or halogen;

$R_{14b}$ is hydrogen, hydroxy, lower alkyl, lower alkenyl, phenyl, phenylloweralkyl, lower alkoxy, or lower alkanoyloxy,;

$R_{16}$ is hydrogen or $R_{16}$ can be ketone provided that $R_{12}$ is hydrogen;

$R_{24}$ is hydrogen or loweralkoxy;

$R_{25}$ is hydrogen;

and the broken line represents a single or double bond between carbons 24 and 25;

provided that the various R groups are not such that the compounds paraherquamide, 24,25-dihydro-paraherquamide, 14-deoxyparaherquamide, and 14-deoxy-14-demethyl-paraherquamide are defined.

More preferred compounds of this invention are realized when:

$R_1$ is hydrogen or substituted benzenesulfonyl;

$R_5$ is hydrogen $R_{12}$ is hydrogen $R_{14a}$ is hydrogen, hydroxy, lower alkoxy, lower alkenylloweralkyloxy, lower alkynylloweralkyl alkyloxy, lower alkanoyloxy, polyalkoxyalkyloxy, triloweralkylsiloxy, or halogen;

$R_{14b}$ is hydrogen, lower alkyl, lower alkenyl, or phenylloweralkyl;

$R_{16}$ is hydrogen;

$R_{24}$ is hydrogen or loweralkoxy,;

$R_{25}$ is hydrogen; and the broken line represents a single or double bond between carbons 24 and 25;

provided that the various R groups are not such that the compounds paraherquamide, 24,25-dihydro-paraherquamide, 14-doxyparaherquamide, and 14-doxy-14-demethyl-paraherquamide are defined.

The most preferred compounds of this invention are realized when:

$R_1$ is hydrogen;

$R_5$ is hydrogen;

$R_{12}$ is hydrogen;

$R_{14a}$ is lower alkoxy, lower alkenylloweralkyloxy, or lower alkynlloweralkyloxy $R_{14b}$ lower alkyl or lower alkenyl;

$R_{16}$ is hydrogen;

$R_{24}$ is hydrogen;

$R_{25}$ is hydrogen; and the broken line represents a double bond between carbons 24 and 25.

Examples of preferred compounds of this invention are as follows:

14-O-methyl-paraherquamide
14-O-ethyl-paraherquamide
14-O-butyl-paraherquamide
14-O-benzyl-paraherquamide
14-O-allyl-paraherquamide
14-O-proparpyl-paraherquamide
14-O-methoxymethyl-paraherquamide
14-O-methoxyethoxymethyl-paraherquamide
17-methyl-paraherquamide
17-methylene-paraherquamide
14-O-trimethylsilyl-paraherquamide
14-O-tert-butyldimethylsilyl-paraherquamide
14-O-(N,N'-dimethyl-ureidocarbonyl)-paraherquamide
14-O-acetyl-paraherquamide
14-O-diphenoxyphosphinyl-paraherquamide
14-fluoro-14-deoxy-paraherquamide
17-nor-paraherquamide
24-methoxy-24 25-dihydro-paraherquamide
24-ethoxy-24,25-dihydro-paraherquamide
24--propoxy-24,25-dihydro-paraherquamide
1-N-(p-toluenesulfon-yl)-paraherquamide
1-N-(2,4,6-tri-isopropylbenzene-sulfonyl)-paraherquamide
1-N-(p-methox-y-benzenesulfonyl)-paraherquamide
1-N-(p-bromo-benzenesulfonyl)-paraherquamide
12-oxo-paraherquamide
16-oxo-paraherquamide
17-hydroxy-paraherquamide
14-epi-paraherquamide
17-nor-14-epi-paraherquamide
16,N-seco-paraherquamide 1-N-acetyl-paraherquamide
1-N-methoxycarbonyl-paraherquamide
1-N-(dimethylcarbamoyl)-paraherquamide
15-oxa-16-oxo-14-deoxy-14-methyl-17-chloromethyl-paraherquamide
15-oxa-16-oxo-14-deoxy-14-methyl-17-hydroxymethyl-paraherquamide
15-oxa-16-oxo-14-deoxy-14-methyl-17-formyl-paraherquamide
14-O-trimethylsilyl-24,25-dihydro-paraherquamide
14-O-trimethylsilyl-24-methoxy-24,25-dihydro-paraherquamide
17-nor-24,25-dihydro-paraherquamide
17-methyl-24,25-dihydro-paraherquamide
24,25,26,27,28-penta-nor-paraherquamide
25-hydroxy-25-hydro-24-nor-paraherquamide
25-alpha-fluoro-25-hydro-24-nor-paraherquamide
25-beta-fluoro-25-hydro-24-nor-paraherquamide
6,7-di-O-methyl-24,25,26,27,28-penta-nor-paraherquamide
1-N-methyl-paraherquamide
1-N-allyl-paraherquamide
5-bromo-paraherquamide
5-amino-paraherquamide
5-nitro-paraherquamide
15-oxa-16-oxo-14-deoxy-14-methyl-17 methyl-18 beta-hydro-18-O,30-cyclo-paraherquamide The novel paraherquamide derivatives of this invention are prepared using the following procedures:

The parent structure, paraherquamide, contains a tertiary hydroxyl group at position 14 which can be used to prepare a large series of derivatives. For example, the 14-hydroxyl group can be alkylated or acylated, provided that the NH group at position is protected (see below), to prepare a series of O-alkyl and O-acyl derivatives ($R_{14a}$=alkoxy or acyloxy in structure below). The process employed to protect the 1—NH group during the alkylation or acylation process is to dissolve paraherquamide in a non-nucleophilic solvent such as dichloromethane, chloroform, ethyl, tetrahydrofuran, benzene, and the like and treat the resulting solution with excess diazomethane and silica gel. The desired 2-O-methyl-imidate is isolated and purified using techniques known to those skilled in the art. Additional 2-O-alkyl imidates may be prepared by substituting the appropriate diazoalkane for diazomethane in the process described above. The process for 14-O-alkylation or acylation involves treating a solution of the 2-O-methyl-imidate in a suitable non-nucleophilic solvent such as dimethylformamide, dimethylsulfoxide, ether, tetrahydrofuran, benzene, and the like with a strong base such as sodium hydride, potassium hydride, n-butyllithium, and the like followed by addition of the alkylating or acylating agent. The alkylating agent may be an alkyl bromide, an alkyl iodide, or an alkyl sulfonate. The acylating agent may be an acyl chloride, an acyl bromide, an acyl anhydride, a chloroformate ester, or an isocyanate. The mixture is then stirred at temperatures ranging from 0° C. to 50° C. until the alkylation is complete. The product is isolated and purified using techniques known to those skilled in the art. The methyl-imidate protecting group is removed by treating a solution of the alkylation product in a non-nucleophilic water miscible solvent such as tetrahydrofuran, dioxane, dimethoxyethane, dimethylformamide and the like with aqueous acid at temperatures ranging from −20° C. to 25° C. Acids such as hydrochloric, sulfuric, hydrobromic, trifluoroacetic and phosphoric are acceptable. Hydrochloric acid is preferred.

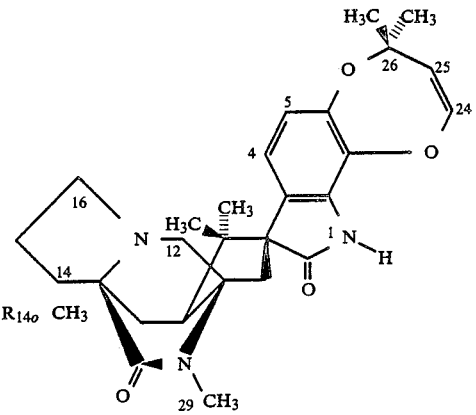

The 14-hydroxyl group may also be substituted with silicon or phosphorus groups to prepare additional 14-O-substituted derivatives ($R_{14a}$=silyloxy or phosphoryloxy in structure above). Because of the greater affinity of these elements for oxygen as opposed to nitrogen these substituents may be attached in a direct procedure under either neutral or basic conditions without the need for a nitrogen protecting group. The trimethylsilyl group is attached to the 14-oxygen under neutral conditions simply by treating a solution of paraherquamide in a dipolar aprotic solvent such as dimethylformamide or dimethylsulfoxide with bis(trimethylsilyl)-trifluoroacetamide at temperatures ranging from 0° C. to 50° C. for 4 to 48 hours. The product is then isolated and purified using techniques known to those skilled in the art. The process for attaching silyl or phosphoryl groups under basic conditions involves treating a solution of paraherquamide in a non-nucleophilic solvent such as tetrahydrofuran, ether, benzene and the like with a strong base such as potassium hydride, sodium hydride, or butyllithium and the like followed by the silylating or phosphorylating agent. Silylating agents such as silyl chlorides, silyl sulfonates, silyl amines, and silyl amides are acceptable. Silyl chlorides are preferred. Phosphorylating agents such as alkyl-chlorophosphates and alkyl-chloro-thiophosphates are acceptable. The mixture is stirred at temperatures ranging from 0° C. to 50° C. for 4 to 48 hours. The product is then isolated and purified using techniques known to those skilled in the art.

The 14-hydroxyl group may also be replaced with a halogen by treating paraherquamide with a suitable halogenating reagent. The process for replacing the hydroxyl group with fluorine involves treating a solution of paraherquamide in a non-nucleophilic solvent such as dichloromethane, chloroform, ether, tetrahydrofuran, benzene and the like with diethylamino-sulfurtrifluoride (DAST) at temperatures ranging from −80° C. to 30° C. The product is then isolated and purified using techniques known to those skilled in the art. This reaction also leads to the formation of by-products in which loss of water has occured to form a double bond (between carbons 14 and 17 and between carbons 14 and 15). These by-products can also be isolated and purified using techniques known to those skilled in the art and can then be used as starting materials for preparation of additional derivatives. The exo-olefin isomer (14,17-anhydro-paraherquamide) can be used to prepare 14-oxo-17-nor-paraherquamide which is especially useful for preparing 17-substituted paraherquamide analogs. This is accomplished by selectively cleaving the 14,17-olefin with ozone (after protecting the 24,25-olefin and the aromatic ring against oxidation by reacting them with bromine). The process for cleaving the 14,17-olefin involves dissolving 14,17-anhydroparaherquamide in a halogenated solvent such as dichloromethane, chloroform, or carbon tetrachloride and treating the solution at temperatures ranging from −50° C. to 25° C. with 2 molar equivalents of bromine. Evaporation of the solvent leaves a yellow residue which is redissolved in a water miscible solvent such as methanol, ethanol, isopropanol or the like (methanol is preferred). Aqueous acid such as hydrochloric, sulfuric or hydrobromic is then added and the solution is treated at temperatures ranging from −80° C. to 0° C. with ozone in a stream of oxygen for 0.5 to 5 minutes. Workup involves blowing a stream of nitrogen through the solution for a few minutes followed by sequential treatment with methyl sulfide and zinc dust. The product, which is 5-bromo-14-oxo-17-nor-paraherquamide (structure below), is then isolated and purified using

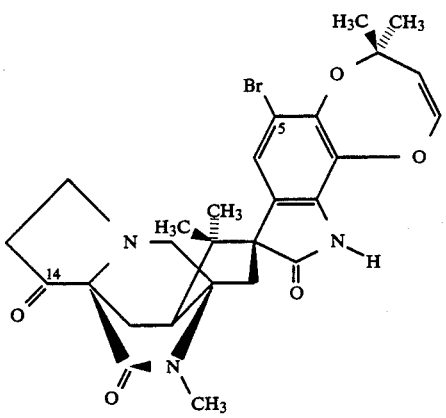

techniques known to those skilled in the art. This compound is used as an intermediate for the preparation of 17-alkylated paraherquamide derivates. The process for preparing these derivatives involves treating a solution of the ketone in a non hydroxylic solvent such as dichloromethane, tetrahydrofuran, ether, hexane, benzene and the like at temperatures ranging from −80° C. to 25° C. with solutions of alkylmagnesium halides in hydrocarbon solvents such as hexane, benzene and the like. Workup involves quenching with water and extraction and affords 5-bromo-17-alkyl-paraherquamide or 5-bromo-17-arylparaherquamide derivatives (and in some cases the corresponding 14-bi-derivatives) which can be purified using techniques known to those skilled in the art. These compounds are then debrominated to afford the final, preferred, products. The debromination procedure involves dissolving the 5-bromo-derivative in a non hydroxylic solvent such as tetrahydrofuran, ether, dimethoxy-ethane, benzene and the like and treating the resulting solution with a strong base such as potassium hydride or sodium hydride at room temperature. The mixture is then treated with an orqanolithium reagent such as tert butyllithium at −78° C. for 0.5 to 5 hours. The product, which is a 17-alkyl- (or aryl)-paraherquamide analog can be purified using techniques known to those skilled in the art. An alternative debromination process which is useful for debromination of 24,25-dihydro derivatives involves removal of the bromine atom by catalytic hydrogenation. The process involves treating a solution of the brominated compound in an alcoholic solvent such as methanol, ethanol, propanol, and the like with hydrogen (either hydrogen has or hydrogen generated in situ from sodium borohydride in the presence of a transition on metal catalyst such as palladium, palladium chloride, platinum and the like at temperatures ranging from 0° C. to 50° C. for 0.5 to 48 hours. The sequence outlined above can also be used to prepare 17-nor-paraherquamide derivatives (replacement of carbon 17 with a hydrogen) by substituting a reducing reagent such as sodium borohydride, lithium aluminum hydride, or the like for the organomagnesium reagent in the reaction with 5-bromo-14-oxo-17-nor-paraherquamide.

The exo-olefin described above can also be used to prepare 17-hydroxy-paraherquamide by reacting first with bromine as described above to protect the 24,25-olefin and the aromatic ring and treating a solution of the resulting tribromide in a water miscible solvent such as tetrahydrofuran, dioxane, and the like at temperatures ranging from 0° C. to 50° C. with a solution of osmium tetroxide and N-methyl-morpholine-N-oxide in an aqueous alcoholic solvent mixture such as methanol, ethanol, isopropanol, or tert-butanol mixed with water for 1 to 10 hours. Aqueous workup followed by treatment of the crude product with zinc dust in aqueous acidic alcohol at room temperature for 0.5 to 5 hours leads to 5-bromo-17-hydroxy-paraherquamide which can be isolated and purified using techniques known to those skilled in the art. Application of the debromination procedure described above to this compound affords 17-hydroxy-paraherquamide which can be used as a starting material for a range of other analogs substituted at carbon 17.

Additional paraharquamide derivatives are obtained by oxidation of the positions (12 and 16) adjacent to the tertiary amine functionality. This can be accomplished either by metal catalyzed air oxidation or by treatment with an oxidizing agent such as bromine, potassium persulfate, and the like. The air oxidation is affected by adding a metal catalyst such as platinum, palladium, and the like to a wet solution of paraherquamide in a non-nucleophilic water miscible solvent such as dioxane (preferred), tetrahydrofuran, dimethylformamide, and the like and bubbling air (or oxygen) through the solution at temperatures ranging from 0° C. to 50° C. for 1 to 48 hours. The product, consisting primarily of 16-oxo-paraherquamide, can then be isolated and purified using techniques known to those skilled in the art. Oxidation of paraherquamide can also be accomplished by treating a solution of paraherquamide in a halogenated solvent such as chloroform, dichloromethane, carbon tetrachloride and the like with 4 molar equivalents of bromine at temperatures ranging from −20° C. to 30° C. for 0.5 to 48 hours and reducing the initial crude product with zinc dust in aqueous acidic tetrahydrofuran. The product mixture which primarily consists of 5-bromo-16-oxo-paraherquamide and some 5-bromo-12-oxo-paraherquamide, can then be isolated and purified using techniques known to those skilled in the art. Debromination of these pure compounds individually using the debromination procedure described above affords 16-oxo-paraherquamide and 12-oxo-paraherquamide, respectively. These compounds can then be used as starting materials for the preparation of additional derivatives.

A novel and unexpected series of derivatives can be accessed by reaction of paraherquamide with phosgene. When a solution of paraherquamide in a non-nucleophilic, non-hydroxylic solvent such as toluene (preferred), benzene, ether, hexane, and the like is treated with phospene and a base such as pyridine, lutidine, triethylamine, and the like at temperatures ranging from 0° C, to 30° C. with vigorous stirring for 0.5 to 48 hours a novel and unexpected product is formed in which the pyrrolidinol ring is broken open and a new 5-membered cyclic urethane is formed. This compound, which is 15-oxa-16-oxo-14-deoxy-14-methyl-17-chloromethyl-paraherquamide (structure below) is useful for the preparation of numerous additional derivatives. For instance, reaction of

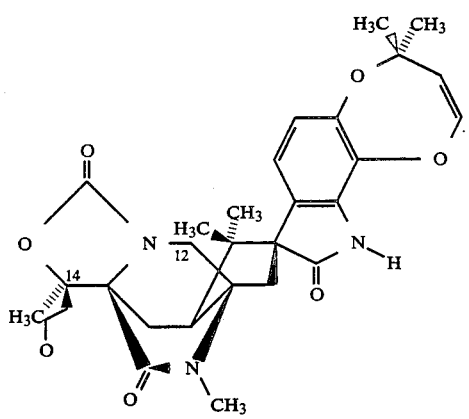

a solution of the chloride in an aprotic solvent such as tetrahydrofuran, ether, benzene, and the like with a powerful reducing agent such as Super Hydride at temperatures ranging from −20° C. to 50° C. for 0.5 to 48 hours results in the formation of three new products which can be isolated and purified using techniques known to those skilled in the art. The major product thus obtained contains an additional ring (structure I below). The other products include one which contains an oxetane ring (structure II below) and 16,N-seco-paraherquamide ($R_{30}=R_N=H$ in substructure C).

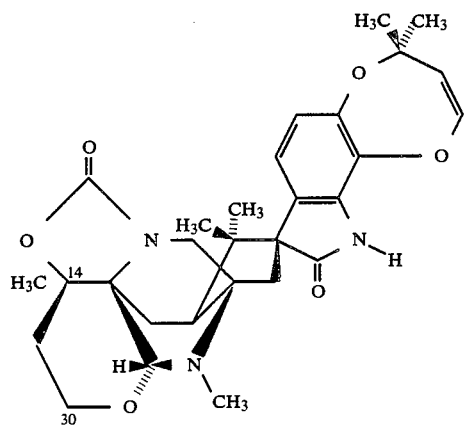

structure I

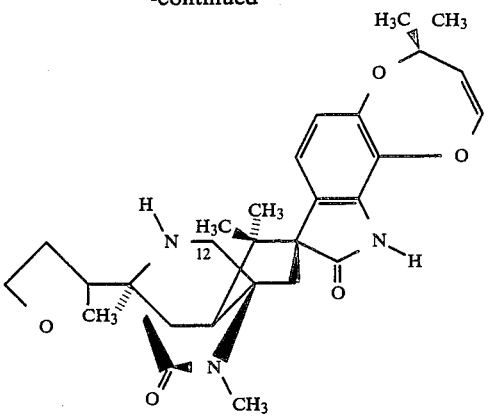

structure II

In addition, the chlorine atom may be replaced with a hydroxyl group by treating a solution of the chloride in a solvent mixture containing 2 to 30% water in an alcholic solvent such as methanol, ethanol, propanol, and the like with a strong base such as 1,8-diazabicyclo[5.4.0]undec-7-ene (DBU) at temperatures ranging from 20° C. to 80° C. for 0.5 to 48 hours. The product, consisting of the corresponding alcohol ($R_{30}=OH$ in substructure B) can be isolated and purified using techniques known to those skilled in the art and is useful for the preparation of numerous additional derivatives. The new hydroxyl group can be alkylated, acylated, silylated, or phosphorylated using the procedures described above for the C-14 hydroxyl group of paraherquamide. In addition, the hydroxyl group may be replaced with fluorine as described above for the C-14 hydroxyl group of paraherquamide. Furthermore, the alcohol may be oxidized to an aldehyde by treating a solution of the alcohol in a halogenated solvent such as dichloromethane chloroform, and the like with an oxidizing agent such as pyridinium chlorochromate (PCC), pyridinium dichromate (PDC) and the like at temperatures ranging from −20° C. to 30° C. for 0.25 to 24 hours. The aldehyde ($R_{30}=oxo$ in substructure B) can be isolated and purified using techniques known to those skilled in the art and is useful for the preparation of still further additional derivatives. Hydrazone and semicarbazone derivatives can be prepared by treating a solution of the aldehyde in an alcoholic solvent such as methanol, ethanol, isopropanol and the like with an appropriate hydrazine or semicarbazide in the presence of an acid catalyst such as acetic acid, hydrochloric acid, sulfuric acid and the like at temperatures ranging from 20° C. to 30° C. for 0.25 to 48 hours.

Additional derivatives of paraherquamide, in which the ring has been cleaved, may be prepared by treating a solution of the aldehyde described above in an organic solvent such as tetrahydrofuran, methanol, ether, benzene, and the like with a strong base such as 1,8-diazabicyclo[5.4.0]undec-7-ene (DBU), potassium tert-butoxide, sodium hydride, and the like at temperatures ranging from 20° C. to 80° C. for 0.5 to 48 hours. The product, consisting of the corresponding ring opened unsaturated aldehyde (structure below) can be isolated and purified using techniques known to those skilled in the art and is

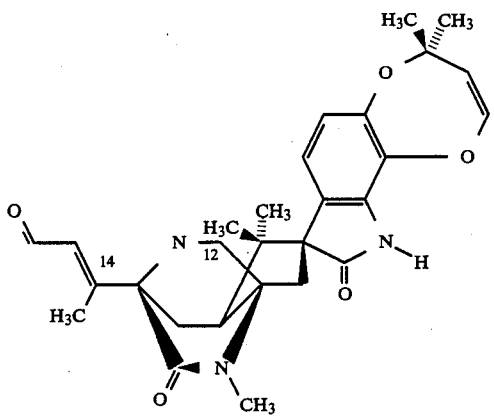

useful for the preparation of additional derivatives. Hydrazones and semicarbazones of the new unsaturated aldehyde may be prepared using the process described above for the saturated aldehyde.

The reaction sequence described above (reaction with phosgene followed by conversion of the chloride to a hydroxyl group) may also be carried out on other paraherquamide analogs. Application of this process to 5-bromo-paraherquamide results in the preparation of 5-bromo-15-oxa-16-oxo-14-deoxy-14-methyl-17-hydroxymethyl-paraherquamide ($R_5$=Br and $R_{30}$=OH in substructure B) This compound can be crystallized to obtain crystals suitable for X-ray diffraction analysis thus allowing the determination of the absolute stereochemistry of paraherquamide.

The aromatic ring of paraherquamide provides an additional site for chemical modification. Thus, a number of paraherquamide analogs with various substituents at position 5 can be readily prepared. The 5-bromo-analog can be prepared by adding 2 molar equivalents of bromine to a solution of paraherquamide in a halogenated solvent such as dichloromethane, chloroform, carbon tetrachloride and the like at temperatures ranging from $-20°$ C. to $25°$ C. for 0.5 to 8 hours. The solvent is then evaporated and the residue dissolved in a water miscible solvent such as tetrahydrofuran, ether, dioxane, and the like and then treated sequentially with 0.1M–3M aqueous potassium dihydrogen phosphate buffer solution (or aqueous acid such as hydrochloric, sulfuric and the like) and zinc dust at temperatures ranging from $0°$ C. to $40°$ C. for 0.5 to 48 hours. This process affords 5-bromo paraherquamide which can be isolated and purified by using techniques known to those skilled in the art. The corresponding 5-chloro- and 5-iodo-analogs may be prepared by substituting the appropriate halogen for bromine in the process outlined above. Nitration of paraherquamide at position 5 can be accomplished by treating a solution of paraherquamide in a dipolar aprotic solvent such as sulfolane, dimethyl sulfoxide, dimethylformamide, and the like with a strong nitrating reagent such as nitronium tetrafluoroborate at temperatures ranging from $-20°$ C. to $50°$ C. for 0.5 to 48 hours. This process affords 5-nitro paraherquamide which can be isolated and purified by using techniques known to those skilled in the art. The nitro derivative thus obtained may be reduced to the corresponding 5-amino analog by treating a solution of the 5-nitro-derivative in a solvent mixture containing a water miscible organic solvent such as tetrahydrofuran, ether, dioxane and the like and an organic acid such as acetic, propionic, and the like with a reducing metal such as zinc, iron, and the like at temperatures ranging from $0°$ C. to $50°$ C. for 1 to 48 hours. This process affords 5 amino-paraherquamide which can be isolated and purified by using techniques known to those skilled in the art. The 5-amino group provides a handle for additional functionalization. Thus, 5-acylamino-analogs may be prepared by treating a solution of the 5-amino derivative in a non-nucleophilic solvent such as tetrahydrofuran, ether, benzene, dichloromathane, and the like with an acylating agent such as an acyl anhydride, an acyl chloride, and the like, and a mild base such as pyridine, triethyl amine, and the like with or without the addition of a nucleophilic catalyst such as 4-dimethylamino pyridine or 4-pyrrolodino-pyridine or the like at temperatures ranging from $0°$ C. to $50°$ C. for 0.5 to 48 hours. This process affords 5-acylaminoparaherquamide analogs which can be isolated and purified by using techniques known to those skilled in the art.

A large series of analogs can be prepared by alkylation or acylation of the 1-NH group of paraherquamide. These derivatives may be easily prepared by sequential treatment of a solution of paraherquamide in an aprotic organic solvent such as tetrahydrofuran, ether, benzene and the like with an excess of a strong base such as potassium hydride (preferred), sodium hydride, butyllithium, potassium tert-butoxide, and the like followed by a suitable alkylating or acylating agent at temperatures ranging from $0°$ C. to $50°$ C. for 0.25 to 48 hours. Suitable alkylating agents include alkyl bromides, alkyl iodides, alkyl sulfonates, and the like. Suitable acylating agents include acyl anhydrides, acyl chlorides, acyl bromides, sulfonyl chlorides, sulfonic anhydrides, isocyanates, carbamoyl chlorides, chloroformates, and the like. This process affords 1-N-substituted paraherquamide analogs which can be isolated and purified by using techniques known to those skilled in the art. Note that these derivatives can be prepared without the need for protection of the hydroxyl group at position 14 since the 1-NH group is significantly more reactive than the 14-OH group under these reaction conditions. However, in some cases 1-N,14-O-disubstituted derivatives are obtained as by-products of the reaction.

An additional series of derivatives can be enerated by modification of the G ring (the 7-membered oxepin ring). One derivative in this area, the 24,25-dihydro-analog, has been previously described in the literature by Yamazaki et al as noted in the background section. Note that the reactions described above for modification of other protions of the paraherquamide structure may also be applied to 24,25-dihydro paraherquamide to prepare the corresponding 24–25,dihydro-analogs, which are new compounds.

Additional G ring modified analogs of paraherquamide may be prepared via the 24,25-dibromide which is easily prepared by treating a solution of paraherquamide in a halogenated solvent such as dichloromethane, chloroform, carbon tetrachloride and the like with 1 molar equivalent of bromine at temperatures ranging from $-20°$ C. to $25°$ C. for 0.25 to 8 hours. This process affords 24,25-dibromo 24,25-dihydro-paraherquamide which can be isolated and purified by using techniques known to those skilled in the art. Note that the 24,25-dichloro analog may be prepared by substituting chlorine for bromine in the process described above. The 24,25-dibromo 24,25-dihydro-paraherquamide described above is a useful intermediate for the preparation of additional derivatives. Thus, treatment of a solution of the dibromide in an alcoholic solvent such as methanol, ethanol, propanol, and the like with a strong base such as 1,8-diazabicyclo[5.4.0]undec-7-ene (DBU) at temperatures ranging from 0° C. to 30° C. for 0.25 to 24 hours. This process affords 24-alkoxy,25-bromo-24,25-dihydro-paraherquamide analogs which can be isolated and purified by using techniques known to those skilled in the art. These 24-alkoxy,25-bromo derivatives can be debrominated by treatment of a solution of the compound in an aprotic organic solvent such as benzene, toluene, hexane, and the like with a tin hydride reducing agent such as tri-butyl tin hydride, tri-phenyl tin hydride and the like with or without the addition of a radical initiator such as azobis-isobutyronitrile (AIBN) at temperatures ranging from 25° C. to 120° C. for 0.5 to 48 hours. This process affords the corresponding 24-alkoxy-paraherquamide derivative (structure below, $R_{24}$=alkoxy) which can be isolated and purified by using techniques known to those skilled in the art.

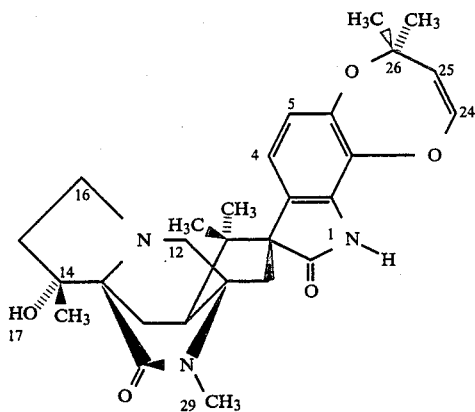

Additional derivatives in which the 7-membered oxepin ring (ring G) has been replaced by a 6-membered dioxane ring can be prepared by ozonolysis of paraherquamide. The process involves treating a solution of paraherquamide in an acidic aqueous alcoholic solvent mixture (mixtures of methanol, ethanol, propanol, and the like with 5 to 20% of 0.5 to 2N aqueous acid such as hydrochloric, sulfuric, phosphoric added are acceptable; methanolic HCl is preferred) with excess ozone gas (in a stream of oxygen) at temperatures ranging from −100° C. to −50° C. for 0.5 to 15 minutes followed by treatment with excess methyl sulfide and stirring at temperatures ranging from 0° C. to 25° C. for 0.5 to 24 hours. This process affords 25-hydroxy-25-hydro-24-nor-paraherquamide ($R_{24}$=OH and $R_{26}$=methyl in substructure E, see also structure below) which can be isolated and purified by using techniques known to those skilled in the art. The ozonolysis procedure described above may also be carried out on 14-O-trimethylsilyl paraherquamide in order to obtain 14-O-trimethylsilyl-25-hydroxy-25 hydro-24-nor-paraherquamide. The presence of the TMS protecting group on the 14-hydroxyl allows derivatization of the newly created hydroxyl group at C-25. Thus, this compound reacts with diethylamino-sulfur-trifluoride (DAST) in a halogenated solvent such as dichloromethane, chloroform, and the like at temperatures ranging from −20° C. to 25° C. for 0.5 to 24 hours. This process affords the corresponding 25-fluoro derivative ($R_{24}$=F and $R_{26}$=methyl in substructure E) (as a mixture of alpha and beta fluoro isomers) which can be isolated and purified by using techniques known to those skilled in the art. The 14-O-trimethylsilyl protecting group may subsequently be removed by treating a solution of the silyl derivative in a non-nucleophilic solvent such as tetrahydrofuran, ether, dioxane, and the like with commercial (Aldrich Chemical Co.) hydrogen fluoride pyridine complex at temperatures ranging from 0° C. to 25° C. for 0.5 to 48 hours. This process affords the corresponding paraherquamide derivative with a free hydroxyl group at C-14 which can be isolated and purified by using techniques known to those skilled in the art (see structure below, $R_{24}$=F and $R_{26}$=methyl).

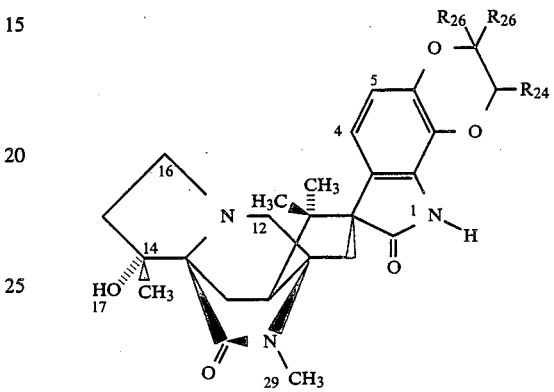

An alternative method for preparing paraherquamide derivatives in in which ring G is a dioxane ring or in which ring G is opened involves alkylation of the catechol derivative ($R_6$=$R_7$=H in substructure F, also see structure below). This useful intermediate can be prepared by treating a solution of paraherquamide in a halogenated solvent such as dichloromethane,

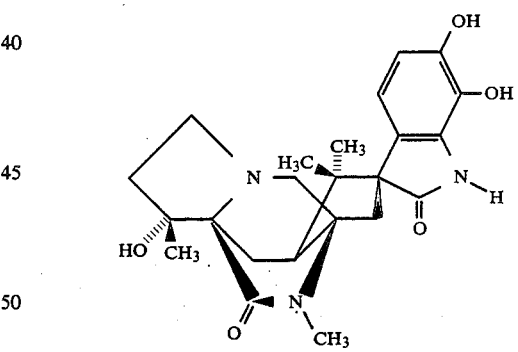

chloroform, and the like with boron trifluoride etherate in the presence of a mercaptan such as thiophenol, ethane thiol, and the like at temperatures ranging from −20° C. to 35° C. for 0.25 to 24 hours followed by methanolysis, concentration and trituration with ether. This process affords the desired catechol derivative which can be isolated and purified by using techniques known to those skilled in the art. As mentioned above, this derivative may be alkylated by treating a solution of the catechol in a dipolar, aprotic solvent such as dimethylformamide, dimethylsulfoxide, and the like with a strong base such as sodium hydride, potassium hydride, and the like followed by a suitable alkylating agent such as an alkyl bromide, alkyl iodide, alkyl sulfonate, and the like at temperatures ranging from 0° C. to 55° C. for 0.5 to 48 hours. When this process is carried out using 1,2-dibromo-ethane as the alkylating agent the desired dioxane derivative ($R_{24}=R_{26}=H$ in substructure E) can be isolated from the reaction mixture and purified by using techniques known to those skilled in the art. Use of other alkylating agents (such as allyl bromide for example) in this procedure allows the preparation of mono and bis alkylated catechol analogs ($R_6=H$ or alkyl, $R_7=$alkyl or H; and $R_6=R_7=$alkyl in substructure F respectively) An additional alkylation method involves reaction of a solution of the catechol in an alcoholic solvent such as methanol, ethanol, and the like with diazomethane at temperatures ranging from 0° C. to 25° C. for 0.5 to 48 hours followed by treatment with a mercaptan such as thiophenol, ethane thiol and the like under basic conditions. This process affords the corresponding 6,7-di-O-methyl derivative ($R_6=R_7=$methyl in substructure F) which can be isolated and purified by using techniques known to those skilled in the art.

The phenolic hydroxyl groups of the catechol derivative may also be acylated by treating a solution of the catechol in a non-nucleophilic solvent such as ether, tetrahydrofuran, dichloromethane, benzene and the like with an appropriate acylating agent such as an acyl anhydride, acyl chloride, chloroformate, isocyanate, and the like with a base such as triethyl amine, pyridine, lutidine, and the like with or without an added nucleophilic catalyst such as 4-dimethylamino-pyridine or 4-pyrrolidino-pyridine at temperatures ranging from 0° C. to 25° C. for 0.5 to 24 hours. This process affords the corresponding 6,7-di-O-acyl catechol derivative ($R_6=R_7=$acyl in substructure F) which can be isolated and purified by using techniques known to those skilled in the art. If desired, 6-mono or 7-mono- acylated derivatives may be prepared by limiting the amount of acylating agent in the process described above.

PREPARATION OF STARTING MATERIALS

The preparation of paraherquamide from the fermentation of *Penicillium paraherqui* is described in Yamazaki et al. supra. Paraherquamide may also be prepared from the fermentation of *Penicillium charlesi* a newly isolated fungus.

Dihydroparaherquamide is prepared from paraherquamide by catalytic hydrogenation over palladium on a carbon support. The analytical characteristics of dihydroparaherquamide are also given in Yamazaki et al.

The novel strain of *Penicillium charlesii* is identified in the culture collection of Merck & Co., as MF 5123. The morphological and cultural characteristics of MF 5123 are as follows:

Morphology of MF 5123

Conidiophores are simple or variously branched with each branch bearing a monoverticillate penicillus and conidial chains forming a long narrow compact column. Conidiophore walls are smooth or nearly so. Conidia are mostly globose, 1.8 m to 2.4 m, slightly roughened.

Cultural characteristics of MF 5123

Czapek Dox agar

Colonies are white, velvety and raised, becoming grey-green with cream colored areas. The reverse side is yellowish-brown and cream. As culture ages, aerial growth becomes grayish brown to brown and a tan soluble pigment diffuses into medium.

Colonies are white becoming grey-green, flat, granular. Reverse side is greenish-brown.

Sabouraud Maltose

Colonies are white becoming brownish green with vectors of yellowish-tan, raised, velvety. Reverse side is dark brown. A brown soluble pigment diffuses into agar.

Yeast-extract Malt-extract agar

Colonies are white becoming gray-green with yellowish areas, raised, velvety. Reverse side is dark brown edged with tan.

Corn agar

Colonies are white becoming gray-green, flat, granular. Reverse side is yellowish. As culture ages, it becomes brown with greenish tones.

A comparison with culture descriptions in *A Manual of the Penicillia* by K. B. Raper and C. Thom and with known cultures show this culture to be a new strain of the known species *Penicillium charlesii*.

A sample of MF 5123, *Penicillium charlesii* has been deposited in the permanent culture collection of the American Type Culture Collection at 12301 Parklawn Drive, Rockville, Mary., 20852 and has been assigned the accession number ATCC 20841.

The above description is illustrative of a strain of *Penicillium charlesii* MF 5123 which can be employed in the production of the instant compound. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

Paraherquamide may be prepared during the aerobic fermentation of a producing strain of *Penicillium charlesii* MF 5123 in either an agitated aqueous medium or in a static solid medium.

Where the nutrient medium is an aqueous medium, suitable media such as those used for the production of many antibiotic substances are suitable for use in this process for the production of paraherquamide.

Such nutrient media contain sources of carbon and nitrogen assimilable by the microrganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, ingredients such as sugars, for example dextrose, sucrose, maltose, lactose, glycerol, corn, millet, wheat, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount between 0.5 and 90% by weight of the medium is satisfactory. These carbon sources may be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, corn, millet, wheat, distillers solubles, cottonseed meal, meat extract and the like, are readily assimilable by *Penicillium charlesii* MF 5123 in the production of the instant compound. The various sources of nitrogen can be used alone or in combination in amounts ranging from 0.2 to 95% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, cadmium, zinc, copper, and the like.

It should be noted that the media described hereinbelow and in the Examples are merely illustrative of the wide variety of media, which may be employed, and are not intended to be limitative.

The following are Examples of media suitable for growing strains of *Penicillium charlesii* MF 5123.

| Medium A | |
|---|---|
| Dextrose | 1.0 g. |
| Soluble starch | 10.0 g. |
| Beef extract | 3.0 g. |
| Yeast autolysate (As ardamine pH available from Yeast Products, Inc., Clifton, N.J.) | 5.0 g. |
| NZ Amine-E (casein hydrolysate-available from Humko-Sheffield-Memphis, Tenn.) | 5.0 g. |
| $MgSO_4.7H_2O$ | 0.05 g. |
| Phosphate Buffer | 2.0 ml. |
| $CaCO_3$ | 0.5 g. |
| Distilled water | 1000 ml. |
| pH 7.0-7.2 | |
| Phosphate Buffer | |
| $KH_2PO_4$ | 91.0 g |
| $Na_2HPO_4$ | 95.0 g |
| Distilled water | 1000 ml |
| pH 7.0 | |
| Medium B | |
| Tomato paste | 20.0 g. |
| Primary yeast | 10.0 g. |
| Dextrin (CPC starch) | 20.0 g. |
| $CoCl_2.6H_2O$ | 0.005 g. |
| Distilled water | 1000 ml |
| pH 7.2-7.4 | |
| Medium C | |
| Corn meal | 20.0 g. |
| Distillers solubles | 10.0 g. |
| Soybean meal | 15.0 g. |
| Sodium citrate | 4.0 g. |
| $CaCl_2.2H_2O$ | 0.5 g. |
| $MgSO_4.7H_2O$ | 0.1 g. |
| $CoCl_2.6H_2O$ | 0.01 g. |
| $FeSO_4.2H_2O$ | 0.01 g. |
| Polyglycol P2000 (Polypropylene glycol mw 2000) | 2.5 mg. |
| Distilled water | 1000 ml. |
| pH 6.5 | |
| Medium D | |
| Lactose | 20.0 g. |
| Distillers solubles | 15.0 g. |
| Autolyzed yeast (Ardamine pH) | 5.0 g. |
| Distilled water | q.s. to 1000 ml |
| pH 7.0 | |
| Medium E | |
| Tomato paste | 40.0 g. |
| Oat Flour | 10.0 g. |
| Distilled water | 1000 ml |
| pH 7.0 | |
| Medium F | |
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard oil | 2.5 g. |
| Distilled water | 1000 ml. |
| pH 6.7 | |
| Medium G | |
| Dextrose | 10.0 g |
| Asparagine | 1.0 g |
| $K_2HPO_4$ | 0.1 g |
| $MgSO_4.7H_2O$ | 0.5 g |
| Yeast Extract | 0.5 g |
| Oat Flour | 10.0 g |
| $CaCO_3$ | 3.0 g |
| Trace Element Mix | 10.0 ml |
| Distilled water | 1000 ml |
| Adjust pH to 7.2 | |
| Trace Element Mix | |
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6MO_4O_{24}.6H_2O$ | 19 mg |
| $ZnSO_4.7H_2O$ | 200 mg |
| Distilled water | 1000 ml |
| Medium H | |
| Medium G | 1000 ml |
| Oat Flour | 10 g |
| pH 7.2 | |

The fermentation employing *Penicilium charlesii* MF 5123 can be conducted at temperatures ranging from about 20° C. to about 40° C. For optimum results, it is most convenient to conduct these fermentations at a temperature in the range of from about 20° C. to about 30° C. Temperatures of about 24°-26° C. are most preferred. The pH of the nutrient medium suitable for producing the instant compounds can vary from about 3.0 to 8.5 with a preferred range of from about 4.0 to 7.0.

Small scale fermentations are conveniently carried out by placing suitable quantities of nutrient medium in a flask employing known sterile techniques, inoculating the flask with either spores or vegetative cellular growth of *Penicillium charlesii* MF 5123 loosely stoppering the flask with cotton and permitting the fermentation to proceed at a constant room temperature of about 25° C. on a rotary shaker at from 0 to 300 rpm for about 2 to 21 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Penicillium charlesii* MF 5123. The fermentation is allowed to continue for from 5 to 20 days while agitating and/or aerating the nutrient medium at a temperature in the range of from about 20° to 28° C. The degree of aeration is dependent upon several factors such as the size of the fermentor, agitation speed, and the like. Generally the larger scale fermentations are agitated at about 95 to 300 RPM and about 2 to 20 cubic feet per minute (CFM) of air.

The fermentation of *Penicillium charlesii* MF 5123 is also successfully carried out in a solid fermentation medium under static, that is, non agitated, conditions. The solid phase aerobic fermentation utilizes the same sources of carbon, nitrogen and inorganic salts as are used for the above-described submerged aqueous fermentation with the primary differences in the constitution of the medium being the quantity of water present. The solid phase fermentations constitute from 30 to 80% by weight of water. Where in comparison with a submerged fermentation medium which may utilize from 10 to 100 g of solid ingredients per liter of medium (1 to 10% w/v), a solid phase medium will contain from 20 to 70% w/v of the solid ingredients.

The solid phase fermentation may be carried out aerobically by maintaining a large ratio of surface area to the mass of the medium. This is readily accomplished by utilizing a 0.3 to 8 cm depth of medium in a fermentation tray or flask. Since the medium is not mechanically agitated, this ensures the presence of sufficient oxygen for growth. Alternatively the solid phase fermentation may be carried out in special trays fitted with sterile gauze for passing air through the solid medium or across the top thereof. Optionally the solid phase fermentation may be carried out with a tight fitting cover.

The fermentation of large scale portions of media may be carried out in stages of increasing quantities of media and it is not necessary that all of the stages be of the same type, that is aqueous or solid. It has been found to be preferable to carry out the initial stages of fermentation in aqueous media and transfer the media to larger scale solid media.

The paraherquamide is found primarily in the mycelium on termination of the *Penicillium charlesii* MF 5123 fermentation and may be removed and separated therefrom as described below.

The separation of the Paraherquamide from the whole fermentation broth and the recovery of said compound is carried out by solvent extraction and application of chromatographic fractionations with various chromatographic techniques and solvent systems.

Paraherquamide has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the paraherquamide as well as other substances lacking the antiparasitic activity of paraherquamide If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the non-polar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, ion exchange resins, dextrans gels and the like, as the chromatographic medium, with various solvents and combinations of solvents as the eluent. Thin layer, high pressure, liquid and preparative layer chromatography may be employed to detect the presence of, and to isolate the instant compound. The use of the foregoing techniques as well as others known to those skilled in the art, will afford purified compositions containing the instant compound.

It has been unexpectedly discovered that the instant paraherquamide derivatives are potent endo- and ecto-antiparasitic agents against parasites particularly helminths, ectoparasites, insects, and acarides, infecting man, animals and plants.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia. Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of this invention may be administered to animals parenterally, for example, by intraruminal, intramuscular, intratracheal, or subcutaneous injection in which the active ingredient is dissolved or dispersed in a liquid carrier vehicle For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

14,17-anhydro-paraherquamide

Diethylaminosulfur trifluoride (0.134 ml, 1.02 mmol, DAST) was added to a cooled (ice bath) solution of paraherquamide (250 mg, 0.51 mmol) and dimethylaminopyridine (25 mg, 0.20 mmol) in 9 ml of dry methylene chloride. The resulting orange solution was stirred at room temperature for thirty minutes then cooled in an ice bath as 4 ml of 5% aqueous sodium bicarbonate was added. The pH of the mixture was then adjusted to 10 by careful addition of 5N aqueous sodium hydroxide solution. The layers were separated and the aqueous layer extracted twice with 3 ml of methylene chloride. The combined organic layers were dried with magnesium sulfate, filtered, and evaporated to a dark yellow oil. Preparative layer chromatography on a 2 mm silica gel plate eluted twice with 40% acetone in hexane afforded 125 mg (52%) of a light yellow oil ($R_f$ 0.33) which was identified by nuclear magnetic resonance and mass spectrometry as 14,17-anhydro-paraherquamide. A second band ($R_f$ 0.42) afforded 12 mg (5%) of a light yellow oil which was identified by nuclear magnetic resonance and mass spectrometry as 14,15-anhydro-paraherquamide. A third band ($R_f$ 0.60) afforded 25 mg (10%) of a light yellow oil which was identified by nuclear magnetic resonance and mass spectrometry as 14-fluoro-14-deoxy-paraherquamide.

Selected $^1H$ NMR (300 MHz, $CDCl_3$) data for 14,17-anhydro-paraherquamide: 6.82 (1H, d, J=8 Hz, $H_4$), 6.69 (1H, d, J=8 Hz, $H_5$), 6.31 (1H, d, J=8 Hz, $H_{24}$), 5.21 & 5.06 (2×1H, 2 br s, $H_{17}$), 4.89 (1H, d, J=8 Hz, $H_{25}$), 3.09 (3H, s, $NCH_3$). $^{13}C$ NMR (75.4 MHz, $CDCl_3$) data: 182.8, 171.4, 146.6, 146.0, 139.0, 135.3, 132.4, 125.2, 120.3, 117.3, 115.0, 108.7, 79.8, 69.8, 65.4, 63.1, 59.6, 52.1 (2C), 46.3, 37.5, 30.7, 30.0, 29.9, 27.6, 26.4, 24.0, 20.8. Selected $^1H$ NMR (300 MHz, $CDCl_3$) data for 14,15-anhydro-paraherquamide: 5.68 (1H, br s, $H_{15}$), 3.05 (3H, s, $NCH_3$), 1.94 (3H, br s, $H_{17}$). Selected $^1H$ NMR (300 MHz, $CDCl_3$) data for 14-fluoro-14-deoxyparaherquamide: 3.06 (3H, s, $NCH_3$), 1.82 (3H, d, J=25 Hz, $H_{17}$). $^{13}C$ NMR (75.4 MHz, $CDCl_3$) 182.9, 169.99 and 169.90 (C-18), 146.1, 139.0, 135.3, 132.4, 125.0, 120.4, 117.3, 115.0, 103.1 and 100.8 (C-14), 79.8, 71.6 and 71.4 (C-13), 65.3, 63.1, 59.3, 51.8, 51.5, 46.4, 37.0, 36.4 and 36.1 (C 15), 29.9, 29.8, 25.8, 23.6, 22.41 and 22.36 (C-19), 20.48, 19.4 and 19.1 (C-17). $^{19}F$ NMR ($CDCl_3$, ppm relative to Freon-11) -133.3 to 133.9 (m, F).

EXAMPLE 2

5-bromo-14-oxo-17-nor-paraherquamide

A solution of bromine (74 mg, 0.46 mmol) in 1 ml of carbon tetrachloride was added to a cold (−20° C.) solution of 14,17-anhydro-paraherquamide (110 mg, 0.23 mmol) in 4 ml of chloroform. The yellow solution was allowed to warm to room temperature and the solvent was evaporated under vacuum. The yellow solid residue was dissolved in 10 ml of 9:1 methanol:2N HCl and the resulting yellow solution cooled to −78° C. (dry ice/acetone bath). A stream of ozone in oxygen gas was bubbled through the solution for 80 seconds followed by a stream of nitrogen gas for one minute Methyl sulfide (0.11 ml, 1.5 mmol) was then added and the mixture allowed to warm to 5° C. Zinc dust (90 mg, 1.4 mmol) was added and the mixture stirred at room temperature for one hour. The mixture was then concentrated under vacuum and the residual oil partitioned between ether (5 ml) and water (3 ml). The pH was adjusted to 10 by careful addition of 5N aqueous sodium hydroxide then the mixture was filtered to remove the white precipitate. The layers were separated and the aqueous layer extracted twice with ether (3 ml) and three times with ethyl acetate (3 ml). The combined extracts were dried with magnesium sulfate, filtered, and evaporated under vacuum. Preparative layer chromatography of the residue on a 0.5 mm silica gel plate eluted with ethyl acetate afforded 46 mg (36%) of a light yellow oil ($R_f$ 0.35) which was identified by nuclear magnetic resonance and mass spectrometry as 5-bromo-14-oxo-14-deoxy-17-nor-paraherquamide.

Selected $^1H$ NMR (300 MHz, $CDCl_3$) data: 7.12 (1H, s, $H_4$), 6.32 (1H, d, J=8 Hz, $H_{24}$), 4.95 (1H, d, J=8 Hz, $H_{25}$), 3.35 (1H, t, J=8 Hz, $H_{16b}$) 3.07 (3H, s, $NCH_3$) 2.65-2.4 (3H, m, $H_{15}+H_{16a}$). $^{13}C$ NMR (75.4 MHz, $CDCl_3$) data 208.1, 182.2, 168.6, 143.7, 138.7, 136.2, 132.1, 125.3, 124.0, 115.4, 110.8, 81.7, 70.1 66.0, 63.1, 59.8, 52.5, 49.7, 46.4, 36.7, 36.5, 29.5 (2C), 25.8, 24.4, 23.6, 20.4.

EXAMPLE 3

5-bromo-17-methyl-paraherquamide

A solution of ethylmagnesium bromide in tetrahydrofuran (0.39 ml of 2M THF solution, 0.78 mmol) was added to a cold (−78° C.) solution of 5-bromo-14-oxo-14-deoxy-17-nor paraherquamide (29 mq, 0.052 mmol) in 2 ml of dry methylene chloride. The resulting solution was stirred at −78° C. for 30 minutes then at room temperature for 2 hours. Water (2 ml) was then added slowly and the mixture centrifuged to separate the layers. The aqueous layer was extracted three times with methylene chloride (4 ml) and the combined extracts dried with magnesium sulfate, filtered and evaporated under vacuum. Preparative layer chromatography of the residual oil on a 0.5 mm silica gel plate eluted with ethyl acetate afforded 17 mg of a colorless oil ($R_f$ 0.41) which was rechromatographed on a 0.25 mm silica gel plate eluted twice with 3.5% methanol in methylene chloride Two bands were extracted from the plate. The first ($R_f$ 0.42) afforded 9 mg (20%) of a colorless oil which was identified by nuclear magnetic resonance and mass spectrometry as 5-bromo-17-methyl-paraherquamide. The second band ($R_f$ 0.30) afforded 3 mg (7%) of a colorless oil which was identified by nuclear magnetic resonance and mass spectrometry as 5-bromo-14-epi-17-methyl-paraherquamide Selected $^1H$ NMR (300 MHz, $CDCl_3$) data for 5-bromo-17-methylparaherquamide: 7.11 (1H, s, $H_4$), 6.33 (1H, d, J=8 Hz, $H_{24}$), 4.95 (1H, d, J=8 Hz, $H_{25}$), 3.04 (3H, s, $NCH_3$), 2.62 (1H, br s, OH), 1.05 (3H, t, J=8 Hz, 17—$CH_3$). Selected $^1H$ NMR (300 MHz, $CDCl_3$) data for 5-bromo-14-epi 17-methyl-paraherquamide: 7.11 (1H, s, $H_4$), 6.48 (1H, br s, OH), 6.33 (1H, d, J=8 Hz, $H_{24}$), 4.95 (1H, d, J=8 Hz, $H_{25}$), 3.09 (3H, s, $NCH_3$), 1.03 (3H, t, J=8 Hz, 17—$CH_3$)

EXAMPLE 4

17-methyl-paraherquamide

Potassium hydride (6 drops of a 25% oil dispersion) was added to a solution of 5-bromo-17-methyl-paraherquamide (15 mg, 0.025 mmol) in 1 ml of dry tetrahydrofuran. The mixture was stirred at room temperature for 15 minutes then cooled to −78° C. A solution of tert-butyllithium in pentane (0.15 ml of 2M pentane solution, 0.30 mmol) was added and the yellow mixture stirred at −78° C. for 2 hours. Water (1 ml) was then added cautiously and the mixture was allowed to warm to ca. 5° C. Ether (2 ml) was added and the layers separated. The aqueous layer was extracted twice with ether (2 ml) and twice with ethyl acetate (2 ml). The combined extracts were dried with magnesium sulfate, filtered, and evaporated under vacuum. Preparative layer chromatoqraphy of the oily residue on a 0.5 mm silica gel plate eluted with ethyl acetate afforded 9 mg (69%) of a colorless oil ($R_f$ 0.30) which was identified by nuclear magnetic resonance and mass spectrometry as 17-methyl-paraherquamide.

Selected $^1$H NMR (300 MHz, CDCl$_3$) data: 6.79 (1H, d, J=8 Hz, H$_4$), 6.66 (1H, d, J=8 Hz, H$_5$), 6.30 (1H, d, J=8 Hz, H$_{24}$), 4.87 (1H, d, J=8 Hz, H$_{25}$), 3.03 (3H, s, NCH$_3$), 2.59 (1H, br s, OH), 1.02 (3H, t, J=8 Hz, 17 CH$_3$).

EXAMPLE 5

14-epi-17-methyl-paraherquamide

Application of the procedure described above (EXAMPLE 4) to 5 mg of 5-bromo-14-epi-17-methyl-paraherquamide afforded a yellow oil which was chromatographed on a 0.25 mm silica gel plate eluted with ethyl acetate to afford 3 mq (70%) of a colorless oil (R$_f$ 0.35) which was identified by nuclear magnetic resonance and mass spectrometry as 14-epi-17-methyl-paraherquamide.

Selected $^1$H NMR (300 MHz, CDCl$_3$) data: 6.78 (1H, d, J=8 Hz, H$_4$), 6.66 (1H, d, J=8 Hz, H$_5$), 6.50 (1H, br s, OH), 6.30 (1H, d, J=8 Hz, H$_{24}$), 4.87 (1H, d, J=8 Hz, H$_{25}$), 3.08 {3H, s, NCH$_3$), 1.02 (3H, t, J=8 Hz, 17—CH$_3$).

EXAMPLE 6

5-bromo-17-nor-paraherquamide

A solution of lithium aluminum hydride in ether (0.14 ml of 1M ether solution, 0.14 mmol) was added to a cold (ice bath) solution of 5-bromo-14-oxo-14-deoxy-17-nor-paraherquamide (39 mg, 0.07 mmol) in 2 ml of dry tetrahydrofuran. The mixture was stirred at 0° C. for 20 minutes then water (1 ml) and ether (2 ml) were added and the layers separated. The aqueous layer was extracted twice with ether (2 ml) then twice with ethyl acetate (2 ml). The combined extracts were dried with magnesium sulfate, filtered and evaporated under vacuum. Preparative layer chromatography of the residue on a 0.5 mm silica gel plate eluted with 7% methanol in methylene chloride afforded 10 mg (26%) of a colorless oil (R$_f$ 0.20) which was identified by nuclear magnetic resonance and mass spectrometry as 5-bromo-17-nor-paraherquamide. A second band (R$_f$ 0.36) afforded 15 mg (38%) of a colorless oil which was identified by nuclear magnetic resonance and mass spectrometry as 5-bromo-14-epi-17-nor-paraherquamide.

Selected $^1$H NMR (300 MHz, CDCl$_3$) data for 5-bromo-17-nor-paraherquamide: 7.10 (1H, s, H$_4$), 6.32 (1H, d, J=8 Hz, H$_{24}$), 4.94 (1H, d, J=8 Hz, H$_{25}$), 4.73 (1H, br t, J=7 Hz, H$_{14}$), 3.04 (3H, s, NCH$_3$). (Selected $^1$H NMR (300 MHz, CDCl$_3$) data for 5 bromo-14-epi-17-nor-paraherquamide: 7.10 (1H, s, H$_4$), 6.34 (1H, d, J=8 Hz, H$_{24}$), 5.52 (1H, d, J=11 Hz, OH), 4.97 (1H, d, J=8 Hz, H$_{25}$), 4.10-4.00 (1H, m, H$_{14}$), 3.08 (3H, s, NCH$_3$).

EXAMPLE 7

17-nor-paraherquamide

Application of the debromination procedure described above (EXAMPLE 4) to 17 mg of 5-bromo-17-nor-paraherquamide and preparative layer chromatography of the crude product on a 0.5 mm silica gel plate eluted with 7% methanol in methylene chloride afforded 4 mg (27%) of a colorless oil (R$_f$ 0.24) which was identified by nuclear magnetic resonance and mass spectrometry as 17-nor-paraherquamide.

Selected $^1$H NMR (300 MHz, CDCl$_3$) data: 6.80 (1H, d, J=8 Hz, H$_4$), 6.66 (1H, d, J=8 Hz, H$_5$). 6.30 (1H, d, J=8 Hz, H$_{24}$). 4.88 (1H, d, J=8 Hz, H$_{25}$), 4.72 (1H, br t, J=7 Hz, H$_{14}$), 3.05 (3H, H$_s$, NCH$_3$).

EXAMPLE 8

14-epi-17-nor-paraherquamide

Application of the debromination procedure described above (EXAMPLE 4) to 21 mg of 5-bromo-14-epi-17-nor-paraherquamide and preparative layer chromatography of the crude product on a 0.5 mm silica gel plate eluted with 50% acetone in hexane afforded 9 mg (50%) of a colorless oil (R$_f$ 0.25) which was identified by nuclear magnetic resonance and mass spectrometry as 14-epi-17-nor-paraherquamide.

Selected $^1$H NMR (300 MHz, CDCl$_3$) data: 6.81 (1H, d, J=8 Hz, H$_4$), 6.68 (1H, d, J=8 Hz, H$_5$), 6.31 (1H, d, J=8 Hz, H$_{24}$), 5.53 (1H, d, J=11 Hz, OH), 4.90 (1H, d, J=8 Hz, H$_{25}$), 4.10-4.00 (1H, m, H$_{14}$), 3.09 (3H, s NCH$_3$).

EXAMPLE 9

5-bromo-17-methylene-paraherquamide

A solution of vinylmagnesium bromide in tetrahydrofuran (1.0 ml of IM THF solution, 1.0 mmol) was added to a cold (−78° C.) solution of 5-bromo-14 oxo-14-deoxy-17-nor-paraherquamide (46 mg. 0.0826 mmol) in 2 ml of dry methylene chloride. The mixture was stirred at −78° C. for 20 minutes then warmed to room temperature and stirred at room temperature for 1 hour. Water (3 ml) was then added followed by chloroform (3 ml) and the layers were separated by centrifugation. The aqueous layer was extracted three times with chloroform (3 ml) and the combined extracts were dried with magnesium sulfate, filtered and evaporated under vacuum. Preparative layer chromatography on a 0.5 mm silica gel plate eluted with ethyl acetate afforded 27 mq (56%) of a white solid (R$_f$ 0.44, mp 230° C. dec.) which was identified by nuclear magnetic resonance as 5-bromo-17-methylene-paraherquamide.

Selected $^1$H NMR (300 MHz, CDCl$_3$) data: 7.08 (1H, s, H$_4$), 6.83 (1H, dd, J=17, 11 Hz, H$_{17}$), 6.30 (1H, d, J=8 Hz, H$_{24}$), 5.46 (1H, dd, J=17, 2 Hz, H$_{30t}$), 5.22 (1H, dd, J=11, 2 Hz, H$_{30c}$), 3.60 (1H, d, J=8 Hz, H$_{25}$), 3.04 (3H, s, NCH$_3$) 2.65 (1H, br s, OH).

EXAMPLE 10

17-methylene-paraherquamide

The debromination procedure described above (EXAMPLE 4) was applied to 5-bromo 17-methyleneparaher-quamide (27 mg, 0.046 mmol). Preparative layer chromatography of the crude product on a 1 mm silica gel plate eluted with ethyl acetate afforded 15 mg (65%) of a light yellow oil (R$_f$ 0.35) which was identified by nuclear magnetic resonance and mass spectrometry as 17-methylene-paraherquamide.

Selected $^1$H NMR (300 MHz, CDCl$_3$) data 6.84 (1H, dd, J=17, 11 Hz, H$_{17}$), 6.78 (1H, d, J=8 Hz, H$_4$), 6.66 (1H, d, J=8 Hz, H$_5$), 6.30 (1H, d, J=8 Hz, H$_{24}$), 5.46 (1H, dd, J=17, 2 Hz, H$_{30t}$), 5.22 (1H, dd, J=11, 2 Hz, H$_{30c}$), 3.60 (1H, d, J=8 Hz, H$_{25}$), 3.04 (3H, s, NCH$_3$) 2.65 (1H, br s, OH). $^{13}$C NMR (75.4 MHz, CDCl$_3$) data: 182.9, 171.6, 146.6, 139.5, 138.7, 135.7, 132.8, 125.5, 120.9, 117.8, 115.5, 115.2, 80.31, 80.27, 73.6, 65.7, 63.6, 59.7, 52.7, 52.0, 46.9, 38.7, 37.5, 30.4, 30.3, 26.4, 24.2, 22.5, 20.9

EXAMPLE 11

14-O-trimethylsilyl-paraherquamide

Bis(trimethylsilyl)trifluoroacetamide (0.16 ml, 0.060 mmol, BSTFA) was added to a solution of paraherquamide (15 mq, 0.030 mmol) in 1 ml of dry dimethylformamide. The resulting solution was stirred at room temperature for 26 hours then evaporated under high vacuum. Preparative layer chromatography of the oily yellow residue on a 0.5 mm silica gel plate eluted with 40% acetone in hexane afforded 16 mg (94%) of a colorless oil ($R_f$ 0.51) which was identified by nuclear magnetic resonance and mass spectrometry as 14-O-trimethylsilyl-paraherquamide.

Selected $^1$H NMR (300 MHz, CDCl$_3$) data: 7.70 (1H, br s, NH), 6.82 (1H, d, J=8 Hz, H$_4$), 6.68 (1H, d, J=8 Hz, H$_5$), 6.32 (1H, d, J=8 Hz, H$_{24}$), 4.89 (1H, d, J=8 Hz, H$_{25}$), 3.02 (3H, s, NCH$_3$), 0.15 (9H, s, OTMS).

EXAMPLE 12

14-O-tert-butyldimethylsilyl-paraherquamide

Potassium hydride (7 drops of a 25% oil dispersion) was added to a solution of paraherquamide (10 mq, 0.020 mmol) in 2 ml of dry tetrahydrofuran. The mixture was stirred at room temperature for 2 hours then tert butyldimethylsilyl chloride (38mg, 0.25 mmol) was added. The mixture was stirred at room temperature for 23 hours then partitioned between methylene chloride (2ml) and 5% aqueous sodium bicarbonate (2 ml). The aqueous layer was extracted twice with methylene chloride (7 ml) and the combined extracts dried with magnesium sulfate, filtered, and evaporated under vacuum. Preparative layer chromatoqraphy of the residue on a 1 mm silica gel plate eluted with 5% methanol in methylene chloride afforded 9 mg (75%) of a white amorphous solid ($R_f$ 0.35) which was identified by nuclear magnetic resonance and mass spectrometry as 14-O-tert-butyldimethylsilyl-paraherquamide.

Selected $^1$H NMR (300 MHz, CDCl$_3$) data: 7.53 (1H, br s, NH), 6.82 (1H, d, J=8 Hz, H$_4$), 6.66 (1H, d, J=8 Hz, H$_5$), 3.02 (3H, s, NCH$_3$), 0.88 (9H, s, Si-tBu), 0.14 and 0.12 (2×3H, 2s, Si-Me).

EXAMPLE 13

14-O-(diphenoxyphosphinyl)-paraherquamide

Potassium hydride (14 drops of a 25% oil dispersion) was added to a solution of paraherquamide (20 mq, 0.040 mmol) in 2 ml of dry tetrahydrofuran. The mixture was stirred at room temperature for 3 hours then diphenylchlorophosphate (130 mg, 0.48 mmol) was added. The mixture was stirred at room temperature for 25 hours then partitioned between methylene chloride (2ml) and 5% aqueous sodium bicarbonate (2 ml). The aqueous layer was extracted twice with methylene chloride (7 ml) and the combined extracts dried with magnesium sulfate, filtered, and evaporated under vacuum. Preparative layer chromatography of the residue on a 1.5 mm silica gel plate eluted with 5% methanol in methylene chloride afforded 15 mg (51%) of a colorless oil ($R_f$ 0.25) which was identified by nuclear magnetic resonance and mass spectrometry as 14-O-(diphenoxyphosphinyl)-paraherquamide.

Selected $^1$H NMR (300 MHz, CDCl$_3$) data: 7.40–7.10 (10 H, m, Ar-H), 6.82 (1H, d, J=8 Hz, H$_4$), 6.70 (1H, d, J=8 Hz, H$_5$).

EXAMPLE 14

24,25-dihydro-paraherquamide

A mixture consisting of 15 mg of 5% palladium on carbon and paraherquamide (30 mg, 0.06 mmol) in 1 ml of methanol was stirred vigorously under an atmosphere of hydrogen for 45 minutes. The reaction mixture was filtered through Celite$^R$ and the filtrate was evaporated under vacuum. Preparative layer chromatography of the residue on a 0.5 mm silica gel plate eluted with 7% methanol in methylene chloride afforded 24 mg (80%) of a colorless oil ($R_f$ 46) which was identified by nuclear magnetic resonance and mass spectrometry as 24,25-dihydroparaherquamide.

Selected $^1$H NMR (300 MHz, CDCl$_3$) data: 4.40–4.30 (2H, m, H$_{24}$), 2.16–2.08 (2H, m, H$_{25}$).

EXAMPLE 15

24,25-dibromo-24,25-dihydro-paraherquamide

A solution of bromine in chloroform (0.4 ml of 0.12 M solution, 0.048 mmol) was added dropwise to a cold (ice bath) solution of paraherquamide (20 mg, 0.06 mmol) in 2 ml of chloroform. The resulting yellow solution was stirred at room temperature for 15 minutes then evaporated under a stream of nitrogen. Preparative layer chromatography of the residue on a 0.5 mm silica gel plate eluted with 5% methanol in methylene chloride afforded 22 mg (83%) of a colorless oil ($R_f$ 0.33) which was identified by nuclear magnetic resonance and mass spectrometry as 24,25-dibromo-24,25-dihydro-paraherquamide (mixture of stereoisomers at C-24 and C-25).

Selected $^1$H NMR (300 MHz, CDCl$_3$) data: 6.95 (1H, d, J=8 Hz, H$_4$), 6.66 (1H, d, J=8 Hz, H$_5$), 6.64 (1H, d, J=8 Hz, H$_{24}$), 4.46 (1H, d, J=8 Hz, H$_{25}$), 3.07 (3H, s, NCH$_3$).

EXAMPLE 16

24-methoxy-24,25-dihydro paraherquamide

A solution of bromine in chloroform (0.6 ml of 0.12 M solution, 0.072 mmol) was added dropwise to a cold (ice bath) solution of paraherquamide (30 mg, 06 mmol) in 2 ml of chloroform. The resulting yellow solution was stirred at room temperature for 10 minutes then at 0° C. for 20 minutes then evaporated under a stream of nitrogen. The yellow solid residue was dissolved in 2 ml of methanol then 1,8-diazabicyclo[5.4.0]undec-7-ene (DBU, 0.015 ml, 0.10 mmol) was added. The solution was stirred at room temperature for 90 minutes then evaporated under vacuum. Preparative layer chromatography of the residue on a 1.0 mm silica gel plate eluted with 5% methanol in methylene chloride afforded 32 mg (87%) of a colorless oil ($R_f$ 0.24) which was identified by nuclear magnetic resonance and mass spectrometry as 24-methoxy-25-bromo-24,25-dihydro-paraherquamide.

Selected $^1$H NMR (300 MHz, CDCl$_3$) data: 5.10 (1H, d, J=6 Hz, H$_{24}$), 4.16 (1H, d, J=6 Hz, H$_{25}$), 3.60 (3H, s, OCH$_3$), 3.06 (3H, s, NCH$_3$).

The 24-methoxy-25-bromo-24,25-dihydro- paraherquamide thus obtained was dissolved in 2 ml of dry toluene then tributyltin hydride (0.12 ml, 0.45 mmol) was added. The solution was stirred at 100° C. for 16 hours then evaporated under vacuum. Preparative layer chromatography of the residue on a 2.0 mm silica gel plate eluted with 5% methanol in methylene chloride afforded 25 mq (78% yield from paraherquamide) of a colorless oil (R$_f$0.22) which was identified by nuclear magnetic resonance and mass spectrometry as 24-methoxy-24,25-dihydro-paraherquamide (mixture of stereoisomers at C-24).

Selected $^1$H NMR (300 MHz, CDCl$_3$) data for major stereoisomer: 5.21 (1H, dd, J=8, 3 Hz, H$_{24}$), 3.58 (3H, s, OCH$_3$), 3.06 (3H. s. NCH$_3$).

EXAMPLE 17

24-propoxy-24,25-dihydro-paraherquamide

Substitution of propanol for methanol in the procedure described above for 24-methoxy-24,25-dihydro-paraherquamide (EXAMPLE 16) and application of the modified procedure to 20 mg of paraherquamide afforded a tan residue. Preparative layer chromatography of the crude product on a 0.5 mm silica gel plate eluted with 5% methanol in methylene chloride afforded 10 mg (45%) of a colorless oil (R$_f$0.32) which was identified by nuclear magnetic resonance and mass spectrometry as 24-propoxy-24,25-dihydro-paraherquamide (mixture of stereoisomers at C-24).

Selected $^1$H NMR (300 MHz, CDCl$_3$) data for major stereoisomer: 5.30 (1H, dd, J=8, 3 Hz, H$_{24}$), 3.95–3.82 and 3.60–3.45 (2×1H, 2m, OCH$_2$), 0.93 (3H, t, J=7 Hz, Et-CH$_3$).

EXAMPLE 18

1-N-methyl paraherquamide

Potassium hydride (80 mg of a 25% oil dispersion) was added to a solution of paraherquamide (30 mg, 0.060 mmol) in 2 ml of dry tetrahydrofuran. The solution was stirred at room temperature for 2 hours then iodomethane (0.038 ml, 0.6 mmol) was added. The mixture was stirred at room temperature for 5 minutes then partitioned between water (2 ml) and methylene chloride (3 ml). The layers were separated and the aqueous layer extracted with methylene chloride (2 ml). The combined extracts were dried with magnesium sulfate, filtered, and evaporated under vacuum. The residual oil was chromatographed on a 1.0 mm silica gel plate eluted twice with 40% acetone in hexane. Two bands were isolated and characterized. The first band (R$_f$0.35) afforded 20 mg (66%) of a colorless oil which was identified by nuclear magnetic resonance and mass spectrometry as 1-N-methyl-paraherquamide. The second band (R$_f$0.41) afforded 10 mg (33%) of a colorless oil which was identified by nuclear magnetic resonance and mass spectrometry as 1-N,14-O-dimethyl-paraherquamide.

Selected $^1$H NMR (300 MHz, CDCl$_3$) data for 1-N-methyl-paraherquamide: 6.82 (1H, d, J=8 Hz, H$_4$), 6.70 (1H, d, J=8 Hz, H$_5$), 3.40 (3H, s, NCH$_3$), 3.05 (3H, s, NCH$_3$), 2.66 (1H, br s, OH). $^{13}$C NMR (75.4 MHz, CDCl$_3$) data: 181.2, 160.4, 147.4, 139.3, 137.9, 134.1, 125.7, 120.2, 117.5, 116.4, 79.6, 78.1, 71.3, 65.4, 61.8, 59.4, 52.0, 51.3, 46.6, 38.2, 37.3, 29.9, 29.6, 29.2, 26.1, 23.8, 22.3, 20.8 19.3.

Selected $^1$H NMR (300 MHz, CDCl$_3$) data for 1-N,14-O-dimethyl-paraherquamide: 6.83 (1H, d, J=8 Hz, H$_4$), 6.70 (1H, d, J=8 Hz, H$_5$), 3.42 (3H, s, NCH$_3$), 3.26 (3H, s, OCH$_3$), 3.06 (3H, s, NCH$_3$)

EXAMPLE 19

1-N benzyl-paraherquamide

Potassium hydride (75 mg of a 25% oil dispersion) was added to a solution of paraherquamide (15 mg, 0.030 mmol) in 1 ml of dry tetrahydrofuran. The solution was stirred at room temperature for 2 hours then benzyl bromide (0.025 ml, 0.21 mmol) was added. The mixture was stirred at room temperature for 3 hours then partitioned between water (1 ml) and methylene chloride (1 ml). The layers were separated and the aqueous layer extracted with methylene chloride (2 ml). The combined extracts were dried with magnesium sulfate, filtered, and evaporated under vacuum. The residual oil was chromatographed on a 1.0 mm silica gel plate eluted with 7% methanol in methylene chloride. Two bands were isolated and characterized. The first band (R$_f$0.50) afforded 12 mg (67%) of a colorless oil which was identified by nuclear magnetic resonance and mass spectrometry as 1-N-benzyl paraherquamide. The second band (R$_f$0.64) afforded 3 mg (15%) of a colorless oil which was identified by nuclear magnetic resonance and mass spectrometry as 1-N,14-O-dibenzyl-paraherquamide.

Selected $^1$H NMR (300 MHz, CDCl$_3$) data for 1-N-benzyl-paraherquamide: 7.32–7.18 (5H, m, Ar-H), 6.86 (1H, d, J=8 Hz, H$_4$), 6.71 (1H, d, J=8 Hz, H$_5$), 5.17 and 5.05 (2×1H, 2d, J=16 Hz, ArCH$_2$N), 3.07 (3H, s, NCH$_3$), 2.65 (1H, br s, OH), 1.65 (3H, s, H$_{17}$). Selected $^1$H NMR (300 MHz, CDCl$_3$) data for 1-N,14-O-dibenzyl-paraherquamide: 7.40–7.18 (5H, m, Ar-H), 6.87 (1H, d, J=8 Hz, H$_4$), 6.71 (1H, d, J=8 Hz, H$_5$), 5.18 and 5.06 (2×1H, 2d, J=16 Hz, ArCH$_2$N), 4.68 and 4.60 (2×1H, 2d, J=13 Hz, ArCH$_2$O), 3.07 (3H; s, NCH$_3$), 1.75 (3H, s, H$_{17}$)

EXAMPLE 20

1-N-(dimethylcarbamoyl)-paraherquamide

Potassium hydride (50 mg of a 25% oil dispersion) was added to a solution of paraherquamide (15 mg, 0.030 mmol) in 1 ml of dry tetrahydrofuran. The solution was stirred at room temperature for 2 hours then dimethylcarbamyl chloride (0.028 ml, 0.30 mmol) was added. After 3 hours at room temperature an additional 0.25 ml of dimethylcarbamyl chloride was added. The mixture was stirred at room temperature for an additional 18 hours then partitioned between 5% aqueous sodium bicarbonate (1 ml) and methylene chloride (1 ml). The layers were separated and the aqueous layer extracted with methylene chloride (2 ml). The combined extracts were dried with magnesium sulfate, filtered, and evaporated under vacuum. Preparative layer chromatography of the residue on a 0.5 mm silica gel plate eluted with 50% acetone in hexane afforded 16 mg (93%) of a colorless oil (R$_f$0.36) which was identified by nuclear magnetic resonance and mass spectrometry as 1-N-(dimethylcarbamoyl)-paraherquamide.

Selected $^1$H NMR (300 MHz, CDCl$_3$) data: 6.84 (2H, s, H$_4$ and H$_5$), 3.07 (3H, s, NCH$_3$), 3.04 (3H, s, NCH$_3$), 2.96 (3H, s, NCH$_3$), 2.62 (1H, br s, OH).

EXAMPLE 21

1-N-acetyl-paraherquamide

Potassium hydride (14 drops of a 25% oil dispersion) was added to a solution of paraherquamide (20 mg, 0.040 mmol) in 2 ml of dry tetrahydrofuran. The solution was stirred at room temperature for 2 hours then acetic anhydride (0.040 ml, 0.42 mmol) was added. The mixture was stirred at room temperature for 22 hours then partitioned between 5% aqueous sodium bicarbonate (2 ml) and methylene chloride (3 ml). The layers were separated and the aqueous layer extracted twice with methylene chloride (7 ml). The combined extracts were dried with magnesium sulfate, filtered, and evaporated under vacuum. Preparative layer chromatography of the residue on a 1.0 mm silica gel plate eluted with 5% methanol in methylene chloride afforded 16 mg (74%) of a colorless oil ($R_f$ 0.34) which was identified by nuclear magnetic resonance and mass spectrometry as 1-N-acetyl-paraherquamide.

Selected $^1$H NMR (300 MHz, CDCl$_3$) data: 6.92 (1H, d, J=8 Hz, H$_4$), 6.86 (1H, d, J=8 Hz, H$_5$), 3.05 (3H, s, NCH$_3$), 2.64 (1H, br s, OH), 2.60 (3H, s, NCOCH$_3$). $^{13}$C NMR (75.4 MHz, CDCl$_3$) data: 181.6, 171.2, 168.8, 148.4, 140.9, 139.0, 130.5, 125.4, 120.4, 120.0, 115.7, 79.8, 78.1, 71.2, 65.3, 63.6, 59.2, 52.0, 51.7, 48.0, 38.1, 37.5, 30.0, 29.8, 26.4, 26.0, 23.8, 22.3, 20.5, 19.2.

EXAMPLE 22

1-N-(methoxycarbonyl)-paraherquamide

Potassium hydride (20 drops of a 25% oil dispersion) was added to a solution of paraherquamide (25 mg, 0.051 mmol) in 3 ml of dry tetrahydrofuran. The solution was stirred at room temperature for 2 hours then methyl chloroformate (0.60 ml, 0.78 mmol) was added. The mixture was stirred at room temperature for 6 hours then partitioned between 5% aqueous sodium bicarbonate (2 ml) and methylene chloride (3 ml). The layers were separated and the aqueous layer extracted twice with methylene chloride (7 ml). The combined extracts were dried with magnesium sulfate, filtered, and evaporated under vacuum. Preparative layer chromatography of the residue on a 1.5 mm silica gel plate eluted with 5% methanol in methylene chloride afforded 22 mg (74%) of a colorless oil ($R_f$ 0.30) which was identified by nuclear magnetic resonance and mass spectrometry as 1-N-(methoxycarbonyl)-paraherquamide.

Selected $^1$H NMR (300 MHz, CDCl$_3$) data: 6.85 (2H, s, H$_4$+H$_5$), 6.30 (1H, d, J=8 Hz, H$_{24}$), 4.87 (1H, d, J=8 Hz, H$_{25}$), 3.98 (3H, s, OCH$_3$), 3.05 (3H, s, NCH$_3$), 1.65 (3H, S, H$_{17}$).

EXAMPLE 23

1-N-(p-toluenesulfonyl)-paraherquamide

Potassium hydride (60 mg of a 25% oil dispersion was added to a solution of paraherquamide (15 mg, 0.030 mmol) in 1 ml of dry tetrahydrofuran. The solution was stirred at room temperature for 2 hours then p-toluenesulfonyl chloride (58 mg, 0.30 mmol) was added. The mixture was stirred at room temperature for 45 minutes then partitioned between 5% aqueous sodium bicarbonate (1 ml) and methylene chloride (1 ml). The layers were separated and the aqueous layer extracted with methylene chloride (2 ml). The combined extracts were dried with magnesium sulfate, filtered, and evaporated under vacuum. Preparative layer chromatography of the residue on a 1.0 mm silica gel plate eluted with 7% methanol in methylene chloride afforded 10 mg (51%) of a colorless oil ($R_f$ 0.43) which was identified by nuclear magnetic resonance and mass spectrometry as 1-N-(p-toluenesulfonyl)-paraherquamide.

Selected $^1$H NMR (300 MHz, CDCl$_3$) data: 8.13 (2H, d, J=8 Hz, Ar-H), 7.37 (2H, d, J=8 Hz, Ar-H), 6.84 (1H, d, J=8 Hz, H$_4$), 6.79 (1H, d, J=8 Hz, H$_5$), 3.01 (3H, s, NCH$_3$), 2.61 (1H, br s, OH).

EXAMPLE 24

5-bromo-paraherquamide

A solution of bromine in carbon tetrachloride (2.0 ml of a 0.12M solution, 0.24 mmol) was added to a cold (ice bath) solution of paraherquamide (60 mg, 0.12 mmol) in 6 ml of chloroform. The yellow solution was stirred at room temperature for 70 minutes then 5 ml of 5% aqueous sodium bicarbonate was added. The layers were separated and the aqueous layer was extracted with methylene chloride (4 ml). The combined organic layers were dried with magnesium sulfate, filtered and evaporated under vacuum. The residue was dissolved in 5 ml of tetrahydrofuran then zinc dust (80 mg, 1.2 mmol) was added followed immediately by 1 ml of 1M aqueous potassium dihydrogen phosphate. The mixture was stirred at room temperature for 15 hours then 4 ml of 5% aqueous sodium bicarbonate was added. The mixture was extracted three times with ether (5 ml) and the combined extracts were dried with magnesium sulfate, filtered and evaporated under vacuum. Preparative layer chromatography of the residue on a 1.5 mm silica gel plate eluted with 50% acetone in hexane afforded 37 mg (53%) of an amorphous white solid ($R_f$ 0.33) which was identified by nuclear magnetic resonance and mass spectrometry as 5-bromo-paraherquamide.

Selected $^1$H NMR (300 MHz, CDCl$_3$) data: 8.59 (1H, br s, NH), 7.10 (1H, s, H$_4$), 6.34 (1H, d, J=8 Hz, H$_{24}$), 4.95 (1H, d, J=8 Hz H$_{25}$), 3.03 (3H, s NCH$_3$). $^{13}$C NMR data (75.4 MHz, CDCl$_3$): 182.1, 171.4, 143.6, 138.6, 136.0, 132.0, 125.5, 124.0, 115.4, 110.7, 81.7, 78.1, 71.4, 65.3, 63.2, 59.1, 51.9, 51.6, 46.8, 38.2, 37.2, 29.6 (2C), 26.0, 23.8, 22.3, 20.6, 19.2.

EXAMPLE 25

5-bromo-16-oxo-paraherquamide

A solution of bromine (260 mg, 1.6 mmol) in 1 ml of carbon tetrachloride was added to a cold (ice bath) solution of paraherquamide (200 mg, 0.40 mmol) in 5 ml of chloroform. The mixture was stirred at room temperature for 75 minutes then cooled in an ice bath as 4 ml of 5% aqueous sodium bicarbonate was added followed by sufficient 5N aqueous sodium hydroxide to raise the pH of the solution to 10. The layers were separated and the aqueous layer extracted three times with methylene chloride (3 ml). The combined extracts were dried with magnesium sulfate, filtered and evaporated under vacuum. The residue was dissolved in 10 ml of tetrahydrofuran then zinc dust (265 mg, 4.0 mmol) was added followed immediately by 2 ml of 1M aqueous potassium dihydrogen phosphate. The mixture was stirred at room temperature for 17 hours then 4 ml of 5% aqueous sodium bicarbonate was added. The pH was adjusted to 10 with 1N sodium hydroxide then the mixture was extracted three times with ether (5 ml). The combined extracts were dried with magnesium sulfate, filtered and evaporated under vacuum. Flash column chromatography of the residue on silica gel (18 cm of 230–400 mesh silica gel in a 40 mm column) eluted with 50% acetone in hexane afforded 2 fractions. The first fraction was a white solid (103 mg, 43%, mp >210 dec.) which was identified by nuclear magnetic resonance and mass spectrometry as 5-bromo-16-oxo-paraherquamide. The second fraction was an oil which contained several impurities. Preparative layer chromatography of this second fraction on a 0.5 mm silica gel plate eluted with ethyl acetate afforded 14 mg (6%) of an amorphous white solid which was identified by nuclear magnetic resonance and mass spectrometry as 5-bromo-12-oxo-paraherquamide.

(Selected $^1$H NMR (300 MHz, CDCl$_3$) data for 5 bromo-16-oxo-paraherquamide: 7.80 (1H, br s, NH), 7.12 (1H, s, H$_4$), 6.33 (1H, d, J=8 Hz, H$_{24}$), 4.96 (1H, d, J=8 Hz, H$_{25}$), 3.66 and 3.55 (2×1H, 2d, J=12 Hz, H$_{12}$), 3.02 (3H, s, NCH$_3$), 2.77 and 2.53 (2×1H, 2d, J=17 Hz, H$_{15}$), 1.84 (3H, s, H$_{17}$). $^{13}$C NMR (75.4 MHz, CDCl$_3$) data for 5-bromo-16-oxo-paraherquamide: 181.5, 172.8, 170.1, 143.8, 138.5. 136.1, 131.9, 124.7, 124.1, 115.5, 111.1. 81.2. 74.8. 69.8, 64.9, 63.2, 52.8, 48.7. 47.2, 46.8. 36.8, 29.7, 29.5. 27.0, 23.7, 22.3, 21.9, 20.6. (Selected $^1$H NMR (300 MHz, CDCl$_3$) data for 5-bromo-12-oxo-paraherquamide: 7.70 (1H, br s, NH), 7.33 (1H, s, H$_4$), 6.31 (1H, d, J=8 Hz, H$_{24}$), 4.94 (1H, d, J=8 Hz, H$_{25}$), 3.70–3.52 (2H, m, H$_{16}$), 3.38 (1H, t, J=9 Hz, H$_{20}$), 3.25 and 2.51 (2×1H, 2d, J=15 Hz, H$_{10}$), 2.97 (3H, s, NCH$_3$), 1.84 (3H, s, H$_{17}$).

EXAMPLE 26

12-oxo-paraherquamide

Application of the debromination procedure described above (EXAMPLE 4) to 11 mg of 5-bromo-12-oxo-paraherquamide and preparative layer chromatography of the crude product on a 0.5 mm silica gel plate eluted with 40% acetone in hexane afforded 7 mg (77%) of a colorless oil (R$_f$ 0.32) which was identified by nuclear magnetic resonance and mass spectrometry as 12 oxo-paraherquamide.

Selected $^1$H NMR (300 MHz, CDCl$_3$) data: 7.45 (1H, br s, NH), 7.00 (1H, d, J=8 Hz, H$_4$), 6.70 (1H, d, J=8 Hz, H$_5$), 6.30 (1H, d, J=8 Hz, H$_{24}$), 4.88 (1H, d, J=8 Hz, H$_{25}$), 3.70–3.52 (2H, m, H$_{16}$), 3.37 (1H, t, J=9 Hz, H$_{20}$), 3.25 and 2.52 (2×1H, 2d, J=15 Hz, H$_{10}$), 2.97 (3H, s, NCH$_3$), 1.84 (3H, s, H$_{17}$).

EXAMPLE 27

16-oxo-paraherquamide

Platinum black (21 mg) was added to a solution of paraherquamide (30 mg, 0.06 mmol) in 3 ml of 50% aqueous dioxane. Air was bubbled through the mixture as it was stirred at room temperature for 5 hours. Additional platinum black was then added and air was bubbled through the mixture for an additional 3 hours. The mixture was stored in the freezer overnight then rewarmed to room temperature. Additional platinum black was again added and air was bubbled through the mixture for an additional 3 hours (total reaction time 11 hours). The mixture was then filtered through Celite ® and evaporated under vacuum. Preparative layer chromatography of the residue on a 1.5 mm silica gel plate eluted with 7% methanol in methylene chloride afforded 26 mg of an amorphous white solid (R$_f$ 0.48) which was not completely pure by analytical layer chromatography. Preparative layer chromatography of this impure material on a 0.25 mm silica gel plate eluted with 50% acetone in hexane afforded 6 mg (19%) of an amorphous white solid (R$_f$ 0.24) which was identified by nuclear magnetic resonance and mass spectrometry as 16-oxo-paraherquamide. Note that 16-oxo-paraherquamide can also be prepared by debromination of 5-bromo 16-oxo-paraherquamide using the debromination procedure described above (EXAMPLE 4).

Selected $_1$H NMR (300 MHz, CDCl$_3$) data for 16-oxo-paraherquamide: 6.81 (1H, d, J=8 Hz, H$_4$), 6.70 (1H, d, J=8 Hz, H$_5$), 6.32 (1H, d, J=8 Hz, H$_{24}$), 4.90 (1H, d, J=8 Hz, H$_{25}$), 3.68 (1H, d, J=12 Hz, H$_{12a}$), 3.54 (1H, d, J=12 Hz, H$_{12b}$), 3.04 (3H, s, NCH$_3$), 2.78 (1H, d, J=16 Hz, H$_{15a}$), 2.52 (1H, d, J=16 Hz, H$_{15b}$). $^{13}$C NMR (75.4 MHz, CDCl$_3$) data: 181.8, 172.9, 170.1, 146.3, 138.9, 135.3, 132.2, 124.2, 120.4, 117.6, 115.2, 79.9, 74.9, 69.7, 64.9, 63.0, 52.6, 48.7, 47.1, 46.4, 36.7, 30.0, 29.7, 26.9, 23.6, 22.2, 21.7, 20.5.

EXAMPLE 28

15-oxa-16-oxo-14-deoxy-14-methyl-17-chloromethyl-paraherquamide

A solution of phosgene in toluene (2.0 ml of a 1.93M toluene solution, 3.86 mmol) was added dropwise to a solution of paraherquamide (80 mg, 0.16 mmol) and dimethylaminopyridine (10 mg, 0.08 mmol) in 2 ml of pyridine then 2 ml of toluene was added. The mixture was stirred vigorously at room temperature for 26 hours then diluted with 4 ml of ether. The mixture was cooled in an ice bath as 4 ml of 5% aqueous sodium bicarbonate was added followed by sufficient 50% aqueous sodium hydroxide to raise the pH to 10. The layers were separated and the aqueous layer extracted four times with ether (3 ml). The combined extracts were dried with magnesium sulfate, filtered, and evaporated under vacuum. Preparative layer chromatography of the residue on a 1.0 mm silica gel plate eluted with 50% acetone in hexane afforded 70 mg of a yellow oil which was not completely pure by analytical layer chromatography. Preparative layer chromatography of this impure material on a 1.0 mm silica gel plate eluted with ether afforded 61 mg (68%) of a colorless oil which was identified by nuclear magnetic resonance and mass spectrometry as 15-oxa-16-oxo-14-deoxy-14-methyl-17-chloromethyl-paraherquamide.

Selected $^1$H NMR (300 MHz, CDCl$_3$) data: 7.70 (1H, br s, NH), 6.81 (1H, d, J=8 Hz, H$_4$), 6.71 (1H, d, J=8 Hz, H$_5$), 3.98 and 3.48 (2×1H, 2d, J=11 Hz, H$_{12}$), 3.74–3.56 (2H, m, CH$_2$Cl). $^{13}$C NMR (75.4 MHz, CDCl$_3$) data: 181.9, 168.9, 155.2, 146.4, 138.8, 135.4, 132.2, 124.0, 120.4, 117.8, 115.3, 83.9, 79.9, 66.7, 64.9, 62.8, 52.3, 49.9, 46.1, 39.5, 39.1, 36.8, 30.0, 29.8, 27.0, 25.0, 23.9, 20.7, 20.4.

EXAMPLE 29

15-oxa-16-oxo-14-deoxy-14-methyl-17-hydroxymethyl-paraherquamide 1,8-diazabicyclo[5.4.0]undec-7-ene (DBU, 0.050 ml, 0.33 mmol) was added to a solution of 15-oxa-16-oxo-14-deoxy-14-methyl-17-chloromethyl-paraherquamide (35 mg, 0.063 mmol) in 1.5 ml of 90% aqueous methanol. The solution was stirred at 55° C. for 4 hours. The mixture was diluted with ether (2 ml) then 1 ml of 5% aqueous sodium bicarbonate was added. The layers were separated and the aqueous layer extracted three times with ether (3 ml) and twice with methylene chloride (2 ml). The combined extracts were dried with magnesium sulfate, filtered, and evaporated under vacuum. Preparative layer chromatography of the residue on a 1.0 mm silica gel plate eluted with 7% methanol in methylene chloride afforded 22 mg (65%) of an amorphous white solid (R$_f$ 0.29) which was identified by nuclear magnetic resonance and mass spectrometry as 15-oxa-16-oxo-14-deoxy-14-methyl 17-hydroxymethyl-paraherquamide. Selected $^1$H NMR (300 MHz, CDCl$_3$) data: 7.65 (1H, br s, NH), 6.82 (1H, d, J=8 Hz, H$_4$), 6.72 (1H, d, J=8 Hz, H$_5$), 3.87 and 3.52 (2×1H, 2d, J=11 Hz, H$_{12}$), 3.98–3.86 and 3.82–3.66 (2×1H, 2m, CH$_2$OH), 2.34 (1H, br s, OH). $^{13}$C NMR (75.4 MHz, CDCl$_3$) data: 182.1, 170.9, 155.5, 146.4, 138.9, 135.4, 132.3, 124.0, 120.3, 117.7, 115.2, 85.3, 79.9, 66.7, 64.9, 62.8, 58.8, 52.3, 49.7, 46.2, 38.0, 36.6, 29.9, 29.8, 27.1, 24.9, 23.7, 21.4, 20.6

EXAMPLE 30

15-oxa-16-oxo-14-deoxy-14-methyl-17-formyl-paraherquamide

Pyridinium chlorochromate (40 mg, 0.19 mmol) was added to a solution of 15-oxa-16-oxo-14-deoxy-14-methyl-17 hydroxymethyl paraherquamide (20 mg, 0.037 mmol) in 1 ml of methylene chloride. The mixture was stirred at room temperature for 1 hour then filtered through Celite ® and evaporated under vacuum. Preparative layer chromatography of the residue on a 1.0 mm silica gel plate eluted with 7% methanol in methylene chloride afforded 10 mg (50%) of a colorless oil (R$_f$ 0.30) which was identified by nuclear magnetic resonance and mass spectrometry as 15-oxa-16-oxo-14-deoxy-14-methyl-17 formyl-paraherquamide. Selected $^1$H NMR (300 MHz, CDCl$_3$) data: 9.79 (1H, br s, CHO), 7.67 (1H, br s, NH), 6.81 (1H, d, J=8 Hz, H$_4$), 6.72 (1H, d, J=8 Hz, H$_5$), 3.87 and 2.98 (2×1H, 2d, J=17 Hz, CH$_2$CO), 3.83 and 3.51 (2×1H, 2d, J=11 Hz, H$_{12}$). $^{13}$C NMR (75.4 MHz, CDCl$_3$) 198.4, 181.7, 169.6, 155.0, 146.3, 138.8, 135.3, 132.2, 124.0, 120.4, 117.7, 115.2, 82.6, 79.9, 65.6, 64.5, 62.8, 52.1, 50.3, 49.6, 46.3, 36.6, 30.0, 29.8, 27.0, 25.1, 23.7, 23.5, 20.5.

EXAMPLE 31

15-oxa-16-oxo-14-deoxy-14-methyl-17-methyl-18-beta-hydro-18-O,30-cyclo-paraherquamide A solution of lithium triethylborohydride in tetrahydrofuran (1.1 ml of a 1.0M THF solution, 1.1 mmol) was added under nitrogen to a cold (0° C.) solution of 15-oxa-16 oxo-14-deoxy-14-methyl-17-chloromethyl paraherquamide (60 mg, 0.1 mmol) in 3 ml of dry tetrahydrofuran. The resulting solution was stirred at room temperature for 7 hours then cooled in an ice bath as 5% aqueous NaHCO$_3$ (3 ml) was added slowly (foaming). The aqueous layer was extracted with ether (7 ml) and dichloromethane (4×7 ml). The combined organic extracts were dried with magnesium sulfate, filtered, and evaporated under vacuum. Preparative layer chromatography of the residue on a 1.5 mm silica gel plate eluted with 5% methanol in dichloromethane afforded one pure compound (R$_f$ 0.26, 13 mg), and another band which was a mixture of two compounds (R$_f$ 0.37, 38 mg). The pure compound was identified by nuclear magnetic resonance and mass spectrometry as 14-O,16-cyclo-16, N-seco-paraherquamide, a novel derivative containing an oxetane ring. The impure band was rechromatographed on a 0.5 mm silica gel plate eluted with 50% acetone in hexane to afford two new derivatives. The first (R$_f$0.32, 23 mg) was identified by nuclear magnetic resonance and mass spectrometry as 15-oxa-16 oxo-14-deoxy-14-methyl-17-methyl-18-beta-hydro-18-O30-cyclo-paraherquamide, a novel derivative in which the chloroethyl side chain of the starting material has cyclized onto the lactam carbonyl which has also been reduced to form a cyclic ether. The second product obtained (R$_f$ 0.44, 13 mg) was identified by nuclear magnetic resonance and mass spectrometry as 16-N seco-paraherquamide, an analog of paraherquamide in which the A-ring has been opened.

Selected $^1$H NMR data (300 MHz, CDCl$_3$) for 15-oxa-16-oxo-14-deoxy-14-methyl-17-methyl-18-beta-hydro-18-O,30-cyclo-paraherquamide: 7.68 (1H, br s, NH), 6.79 (1H, d, J=8 Hz, H$_4$), 6.68 (1H, d, J=8 Hz, H$_5$), 6.28 (1H, d, J=8 Hz, H$_{24}$), 4.87 (1H, d, J=8 Hz, H$_{25}$), 4.00 (1H, s, H$_{18}$), 3.88 (1H, d, J=10 Hz, H$_{12a}$), 3.60 (1H, d, J=10 Hz, H$_{12b}$), 2.71 (3H, s, NCH$_3$). $^{13}$C NMR (75.4 MHz, CDCl$_3$) data: 182.0, 156.6, 146.0, 138.8, 135.2, 132.0, 125.5, 120.7, 117.6, 115.2, 94.5, 80.0, 79.8, 62.5, 62.4, 60.8, 60.6, 53.0, 45.8, 44.2, 36.9, 35.2, 34.3, 30.0, 29.7, 25.1, 24.5, 21.9, 21.0; Selected $^1$H NMR data (300 MHz, CDCl$_3$) for 14O,16-cyclo-16,N seco-paraherquamide: 7.60 (1H, br s, NH), 6.82 (1H, d, J=8 Hz, H$_4$), 6.68 (1H, d, J=8 Hz, H$_5$), 6.32 (1H, d, J=8 Hz, H$_{24}$), 4.89 (1H, d, J=8 Hz, H$_{25}$), 4.65–4.45 (2H, m, H$_{16}$), 3.54 (1H, d, J=11 Hz, H$_{12a}$), 3.07 (3H, s, NCH$_3$), 3.04 (1H, d, J=11 Hz, H$_{12b}$). $^{13}$C NMR (75.4 MHz, CDCl$_3$) data: 182.0, 172.4, 146.9, 138.9, 135.2, 132.3, 124.8, 120.5, 117.3, 115.1, 88.1, 79.8, 66.3, 64.1, 63.3, 63.0, 53.4, 50.9, 46.8, 37.2, 30.2, 30.0, 29.8, 26.5, 25.4, 23.9, 23.6, 20.7; Selected $^1$H NMR data (300 MHz, CDCl$_3$) for 16,N-seco-paraherquamide: 7.90 (1H, br s, NH), 6.81 (1H, d, J=8 Hz, H$_4$), 6.68 (1H, d, J=8 Hz, H$_5$), 6.33 (1H, d, J=8 Hz, H$_{24}$), 4.90 (1H, d, J=8 Hz, H$_{25}$), 3.38 (1H, d, J=11 Hz, H$_{12a}$), 3.08 (3H, s, NCH$_3$), 2.90 (1H, d, J=11 Hz, H$_{12b}$), 1.02 (3H, t, J=7 Hz, H$_{16}$).

EXAMPLE 32

16-nor-14,17-anhydro-17-formyl-paraherquamide 1,8-diazabicyclo[5.4.0]undec-7-ene (DBU, 0.060 ml, 0.40 mmol) was added to a solution of 15-oxa-16-oxo-14-deoxy-14-methyl-17-formyl-paraherquamide (74 mg, 0.14 mmol) in 2 ml of dry tetrahydrofuran and the solution was stirred at room temperature for 30 minutes then partitioned between ether (2 ml) and 5% aqueous NaHCO$_3$. The aqueous layer was extracted with ether (2×4 ml) and dichloromethane (3×4 ml). The combined organic layers were dried with magnesium sulfate, filtered, and evaporated under vacuum. Preparative layer chromatography of the residue on a 1.0 mm silica gel plate eluted with 50% acetone in hexane afforded 51 mg (75%) of a colorless oil (R$_f$ 0.29) which was identified by nuclear magnetic resonance and mass spectrometry as 16-nor-14,17-anhydro 17-formyl-paraherquamide. Selected $^1$H NMR data (300 MHz, CDCl$_3$): 10.14 (1H, d, J=7 hz, CHO), 6.26 (1H, d, J=7 Hz, H$_{17}$), 3.47 (1H, d, J=12 Hz, H$_{12a}$), 3.10 (3H, s, NCH$_3$), 2.97 (1H, d, J=12 Hz, H$_{12b}$), 2.40 (3H, s, H$_{15}$); $^{13}$C NMR (75.4 MHz, CDCl$_3$) data: 191.9, 182.4, 172.5, 161.3, 146.2, 139.0, 135.3, 132.5, 126.3, 124.3, 120.4, 117.4, 115.1, 79.8, 65.6, 64.2, 63.2, 54.4, 51.4, 46.9, 36.8, 30.0, 29.8, 28.3, 27.2, 23.7, 20.4, 16.2.

EXAMPLE 33

15,16-seco 14,17-anhydro-17-formyl-paraherquamide

Iodomethane (0.016 ml, 0.26 mmol) was added to a solution of 16-nor-14,17-anhydro-17-formylparaherquamide (25 mg, 0.05 mmol) and triethylamine (0.015 ml, 0.11 mmol) in 1.5 ml of dry tetrahydrofuran. The solution was stirred at room temperature for 90 minutes then additional iodomethane (0.016 ml, 0.26 mmol) was added. The mixture was stirred at room temperature for an additional 5 hours then additional iodomethane (0.035 ml) was added and the mixture stirred at 55° C. for 23 hours. Analytical TLC then showed that the reaction was complete. The reaction mixture was partitioned between ether (5 ml) and 5% aqueous NaHCO$_3$ (5 ml). The aqueous layer was extracted with ether (2×5 ml) and dichloromethane (3×5 ml). The combined organic layers were dried with magnesium sulfate, filtered, and evaporated under vacuum. Preparative layer chromatography of the residue on a 0.5 mm silica gel plate eluted with 7% methanol in dichloromethane afforded 5 mg (19%) of a colorless oil ($R_f$ 0.59) which was identified by nuclear magnetic resonance and mass spectrometry as 15,16-seco-14,17-anhydro-17-formyl-paraherquamide. Selected $^1$H NMR data (300 MHz, CDCl$_3$): 10.16 (1H, d, J=7 hz, CHO), 6.36 (1H, d, J=7 Hz, H$_{17}$), 3.57 (1H, d, J=12 Hz, H$_{12a}$), 3.11 (3H, s, NCH$_3$), 2.52 (1H, d, J=12 Hz, H$_{12b}$), 2.46 (3H, s, H$_{15}$), 2.16 (3H, s, H$_{16}$).

EXAMPLE 34

14,15-anhydro-16,N-seco-16-tert-butyl-paraherquamide

A solution of tert-butyllithium (0.32 ml of 2.0M pentane solution, 0.64 mmol) was added under nitrogen to a cold (−78° C.) solution of 15-oxa 16-oxo-14-deoxy-14-methyl-17 chloromethyl-paraherquamide (50 mg, 0.09 mmol) in 3 ml of dry tetrahydrofuran. The cold bath was removed and the solution warmed to 0° C. and stirred at 0° C. for 1 hour. Water (2 ml) was then added very carefully dropwise (vigorous reaction) at 0° C. The aqueous layer was extracted with dichloromethane (3×5 ml) and ethyl acetate (3×5 ml) and the combined organic layers dried with magnesium sulfate, filtered, and evaporated under vacuum. Preparative layer chromatography of the residue on a 1.2 mm silica gel plate eluted with eluted with 7% methanol in methylene chloride afforded 36 mg of a colorless oil ($R_f$ 0.37). This impure material was further purified by preparative layer chromatography on a 5 mm silica gel plate eluted with 50% acetone in hexane. Two bands (12 mg, $R_f$ 0.54 and 7 mg, $R_f$ 0.30) were isolated from the plate and were shown by nuclear magnetic resonance and mass spectrometry to be the two olefin isomers (E and Z) of 14,15-anhydro-16,N-seco-16 tert-butyl-paraherquamide.

Selected $^1$H NMR data (300 MHz, CDCl$_3$) for the major olefin isomer: 5.64 (1H, t, J=7 Hz, H$_{15}$), 1.80 (3H, s, H$_{17}$), 0.92 (9H, s, C(CH$_3$)$_3$). Selected $^1$H NMR data (300 MHz, CDCl$_3$) for the minor olefin isomer: 5.60 (1H, t, J=7 Hz, H$_{15}$), 1.88 (3H, s, H$_{17}$), 0.92 (9H, s, C(CH$_3$)$_3$).

EXAMPLE 35

15oxa-16-oxo-14-deoxy-14-methyl-17-formyl-paraherquamide-toluenesulfonyl-hydrazone Glacial acetic acid (0.0011 ml, 0.019 mmol) was added to a solution of p-toluenesulfonhydrazide (11 mg, 0.059 mmol) and 15-oxa-16-oxo-14-deoxy-14-methyl-17-formyl-paraherquamide (21 mg, 0.039 mmol) in 1 ml of dry methanol. The solution was stirred at room temperature for 90 minutes then partitioned between ether (4 ml) and 2% aqueous NaHCO$_3$ (2 ml). The aqueous layer was extracted with ether (3×3 ml) and dichloromethane (4 ml). The combined organic layers were dried with magnesium sulfate, filtered, and evaporated under vacuum. Preparative layer chromatography of the residue on a 0.5 mm silica gel plate eluted with 50% acetone in hexane afforded an impure oil ($R_f$ 0.31). This oil was further purified by preparative layer chromatography on a 0.25 mm silica gel plate eluted with 5% methanol in methylene chloride which afforded 18 mg (65%) of a white amorphous solid which was identified by nuclear magnetic resonance and mass spectrometry as 15-oxa-16-oxo-14-deoxy-14-methyl-17-formyl-paraherquamide-toluenesulfonyl-hydrazone.

Selected $^1$H NMR data (300 MHz, CDCl$_3$): 8.31 (1H, br s, NH), 7.79 (2H, d, J=8 Hz, Ar—H), 7.76 (1H, s, NNH), 7.30 (2H, d, J=8 Hz, Ar—H), 7.26 (1H, t, J=7 Hz, CH=NN), 3.94 (1H, d, J=11 Hz, H$_{12a}$), 3.49 (1H, d, J=11 Hz, H$_{12b}$), 3.33 (1H, dd, J=7, 14 Hz, H$_{17a}$). 2 88 (1H, dd, J=7, 14 Hz, H$_{17b}$), 2.30 (3H, s, ArCH$_3$)

EXAMPLE 36

15-oxa-16-oxo-14-deoxy-14-methyl-17-acetoxymethyl-paraherquamide

Acetic anhydride (0.5 ml) was added to a solution of 15-oxa-16-oxo-14-deoxy-14-methyl-17-hydroxymethyl-paraherquamide (24 mg) and 4-dimethylamino-pyridine (3 mg) in pyridine (0.5 ml). The solution was stirred at room temperature for 30 minutes then cooled in an ice bath as the pH was adjusted to 7 by addition of 5% NaHCO$_3$. The mixture was extracted with methylene chloride (3×5 ml) and ether (2×5 ml) and the combined organic extracts were dried with magnesium sulfate, filtered, and evaporated under vacuum. Preparative layer chromatography of the residue on a 0.5 mm silica gel plate eluted with 50% acetone in hexane afforded two pure compounds. The first product (10 mg, $R_f$ 0.47) was identified by nuclear magnetic resonance and mass spectrometry as 15-oxa-16-oxo-14-deoxy-14-methyl-17-acetoxymethyl-paraherquamide. The second product (10 mg, $R_f$ 0.58) was identified by nuclear magnetic resonance and mass spectrometry as 1-N-acetyl-15-oxa-16-oxo-14-deoxy-14-methyl-17 acetoxymethyl-paraherquamide.

Selected $^1$H NMR data (300 MHz, CDCl$_3$) for 15-oxa-16-oxo-14-deoxy-14-methyl-17-acetoxymethyl-paraherquamide: 7.58 (1H, br s, NH), 6.82 (1H, d, J=8 Hz, H$_4$), 6.72 (1H, d, J=8 Hz, H$_5$), 4.30–4.20 (2H, m, CH$_2$OAc), 2.03 (3H, s, OCOCH$_3$). Selected $^1$H NMR data (300 MHz, CDCl$_3$) for 1-N-acetyl-15-oxa-16-oxo-14-deoxy-14 methyl 17 acetoxymethyl paraherquamide: 6.94 (1H, d, J=8 Hz, H$_4$), 6.86 (1H, d, J=8 Hz, H$_5$), 4.30–4.20 (2H, m, CH$_2$OAc), 2.61 (3H, s, NCOCH$_3$), 2.03 (3H, s, OCOCH$_3$).

EXAMPLE 37

1-N-methyl-15-oxa-16-oxo-14-deoxy-14-methyl-17-methoxymethyl-paraherquamide

Iodomethane (0.005 ml, 0.08 mmol) was added to a mixture of 15-oxa-16-oxo-14-deoxy-14-methyl-17-hydroxymethyl-paraherquamide (30 mg, 0.06 mmol), silver (I) oxide (26 mg, 0.11 mmol), and potassium carbonate (15 mg, 0.11 mmol) in 1 ml of dry dimethylformamide. The mixture was stirred at room temperature for 2 hours then as TLC indicated no reaction an additional 0.005 ml of iodomethane was added and the mixture stirred at 30° C. for an additional 2.5 hours. Additional iodomethane (0.025 ml) was then added and the mixture stirred at room temperature for 2 hours. The mixture was then poured into water (2 ml) and the resulting mixture extracted with ether (2×5 ml) and methylene chloride (3×5 ml). The combined organic layers were dried with magnesium sulfate, filtered, and evaporated under vacuum. Preparative layer chromatography of the residue on a 1.5 mm silica gel plate eluted with 50% acetone in hexane afforded two pure compounds. The first product (7 mg, $R_f$ 0.56) was identified by nuclear magnetic resonance and mass spectrometry as 1-N-methyl-15-oxa-16-oxo-14-deoxy-14-methyl-17-methoxy methyl-paraherquamide. The second product (15 mg, $R_f$ 0.35) was identified by nuclear magnetic resonance and mass spectrometry as 1-N-methyl-15-oxa-16-oxo-14-deoxy-14-methyl-17-hydroxymethyl paraherquamide.

Selected $^1$H NMR data (300 MHz, CDCl$_3$) for 1-N-methyl-15-oxa-16-oxo-14-deoxy -14-methyl-17-methoxy methyl-paraherquamide: 4.40–4.20 (2H, m, CH$_2$O), 3.78 (3H, s, OCH$_3$), 3.41 (3H, s, NCH$_3$), 3.07 (3H, s, NCH$_3$).

Selected $^1$H NMR data (300 MHz, CDCl$_3$) for 1-N-methyl-15-oxa-16-oxo-14-deoxy-14-methyl-17-hydroxy methyl-paraherquamide: 3.97–3.87 and 3.80–3.70 (2H, m, CH$_2$O), 3.41 (3H, s, NCH$_3$), 3.07 (3H, s, NCH$_3$), 2.39 (1H, dd, J=3, 8 Hz, OH).

EXAMPLE 38

5-bromo-15-oxa-16-oxo-14-deoxy-14-methyl-17 hydroxymethyl-paraherquamide

A solution of phosgene in toluene (2.0 ml of a 1.93M toluene solution, 3.86 mmol) was added dropwise to a solution of 5-bromo-paraherquamide (70 mg, 0.12 mmol) and dimethylaminopyridine (10 mg, 0.08 mmol) in 2 ml of pyridine then 2 ml of toluene was added. The mixture was stirred vigorously at room temperature for 65 hours then diluted with 4 ml of ether. The mixture was cooled in an ice bath as 4 ml of 5% aqueous sodium bicarbonate was added followed by sufficient 50% aqueous sodium hydroxide to raise the pH to 10. The layers were separated and the aqueous layer extracted ether (4×3 ml) and methylene chloride (2×3 ml). The combined extracts were dried with magnesium sulfate, filtered, and evaporated under vacuum. Preparative layer chromatography of the residue on a 1.0 mm silica gel plate eluted with 50% acetone in hexane afforded 35 mg of a yellow oil which was not completely pure by analytical layer chromatography. Preparative layer chromatography of this impure material on a 0.5 mm silica gel plate eluted with 50% ethyl acetate in hexane afforded 30 mg (39%) of a colorless oil which was identified by nuclear magnetic resonance and mass spectrometry as 5-bromo-15-oxa-16-oxo-14-deoxy-14-methyl-17-chloromethyl-paraherquamide. This material was dissolved in 2 ml of 90% aqueous methanol then 1,8-diazabicyclo[5.4.0]undec-7 ene (DBU, 0.050 ml) was added. The solution was stirred at 55° C. for 19 hours then partitioned between ether (4 ml) and 5% aqueous NaHCO$_3$ (2 ml). The aqueous layer was extracted with ether (3×3 ml) and the combined organic layers were dried with magnesium sulfate, filtered, and evaporated under vacuum. Preparative layer chromatography of the residue on a 0.5 mm silica gel plate eluted with eluted with 7% methanol in methylene chloride afforded 20 mg (69%) of a colorless oil which was identified by nuclear magnetic resonance and mass spectrometry as 5-bromo-15-oxa-16-oxo-14-deoxy-14-methyl-17-hydroxymethyl-paraherquamide.

Selected $^1$H NMR data (300 MHz, CDCl$_3$): 8.18 (1H, br s, NH), 7.12 (1H, s, H$_4$), 6.32 (1H, d, J=8 Hz, H$_{24}$), 4.96 (1H, d, J=8 Hz, H$_{25}$), 3.97–3.87 and 3.80–3.70 (2H, m, CH$_2$O), 3.86 (1H, d, J=11 Hz H$_{12a}$). 3.54 (1H, d, J=11 Hz, H$_{12b}$), 3.07 (3H, s, NCH$_3$), 2.39 (1H, dd, J=3, 8 Hz, OH).

EXAMPLE 39

17-hydroxy-paraherquamide

A solution of osmium tetroxide (0.36 ml of 0.077M tert butanol solution, 0.030 mmol) was added to a solution of N-methyl-morph-oline-N-oxide (24 mg, 0.20 mmol) in 1 ml of 90% aqueous tert-butanol at room temperature. A solution of 24,25-dibromo- 24,25-dihydro-paraherquamide (87 mg, 0.13 mmol, prepared from 65 mg of paraherquamide using the procedure described above but used without purification) in 1 ml of dry tetrahydrofuran was then added. The mixture was stirred under nitrogen at room temperature for 3.5 hours then 2 ml of 5% aqueous NaHCO$_3$ was added. The aqueous layer was extracted with ether (3×5 ml) and ethyl acetate (3×5 ml). The combined organic layers were dried with magnesium sulfate, filtered, and evaporated under a stream of nitrogen in the hood. The residue was dissolved in 2 ml of 9:1 methanol:2N HCl then zinc dust (65 mg) was added. The mixture was stirred at room temperature for 1 hour then 5% aqueous NaHCO$_3$ (2 ml) and 5% aqueous sodium sulfite (1 ml) were added. The aqueous layer was extracted with ether (3×5 ml) and ethyl acetate (2×5 ml). The combined organic layers were dried with magnesium sulfate, filtered, and evaporated under a stream of nitrogen in the hood. Preparative layer chromatography of the residue on a 1.5 mm silica gel plate eluted twice with 7% methanol in methylene chloride afforded 10 mg of a colorless oil ($R_f$ 0.38) which was identified by nuclear magnetic resonance and mass spectrometry as 17-hydroxy-paraherquamide.

Selected $^1$H NMR data (300 MHz, CDCl$_3$): 7.80 (1H, s, NH), 6.78 (1H, d, J=8 Hz, H$_4$), 6.66 (1H, d, J=8 Hz, H$_5$), 6.30 (1H, d, J=8 Hz, H$_{24}$), 5.32 (1H, br s, OH), 4.88 (1H, d, J=8 hz, H$_{25}$), 3.96–3.80 (2H, m, CH$_2$O), 3.06 (3H, s, NCH$_3$)

EXAMPLE 40

14,17-anhydro-15-hydroxy-paraherquamide

A solution of 14,17-anhydro-paraherquamide (20 mg, 0.04 mmol) and selenium dioxide (10 mg, 0.088 mmol) in 1 ml of ethanol was stirred at room temperature for 40 minutes then at 75° C. for 17.5 hours. The red solution was then cooled to room temperature and partitioned between ether (2 ml) and 5% aqueous NaHCO$_3$. The aqueous layer was extracted with ether (3×2 ml). The combined organic layers were dried with magnesium sulfate, filtered, and evaporated under vacuum. Preparative layer chromatography of the residue on a 5 mm silica gel plate eluted with 7% methanol in methylene chloride afforded two pure compounds (in addition to recovered starting material) which were identified by nuclear magnetic resonance and mass spectrometry as the two isomeric forms (15-alpha and 15-beta) of 14,17-anhydro 15 hydroxy-paraherquamide.

Selected $^1$H NMR data (300 MHz, CDCl$_3$) for the major isomer (5 mg, $R_f$ 0.34): 7.60 (1H, s, NH), 6.82 (1H, d, J=8 Hz, H$_4$), 6.69 (1H, d, J=8 Hz, H$_5$), 6.31 (1H, d, J=8 Hz, H$_{24}$), 5.58 (1H, br s, H$_{17a}$), 5.26 (1H, br s, H$_{17b}$), 4.89 (1H, d, J=8 Hz, H$_{25}$), 4.58 (1H, br s, H$_{15}$), 3.11 (3H, s, NCH$_3$). Selected $^1$H NMR data (300 MHz, CDCl$_3$) for the minor isomer (2 mg, $R_f$ 0.26): 7.40 (1H, s, NH), 6.82 (1H, d, J=8 Hz, H$_4$), 6.69 (1H, d, J=8 Hz, H$_5$), 6.30 (1H, d, J=8 Hz, H$_{24}$). 5.61 (1H, br s, H$_{17a}$), 5.30 (1H, br s, H$_{17b}$), 4.89 (1H, d, J=8 Hz, H$_{25}$), 4.65 (1H, br s, H$_{15}$), 3.07 (3H, s, NCH$_3$).

EXAMPLE 41

14-O-trimethylsilyl-25-hydroxy-25-hydro-24-nor-paraherquamide

Bis(trimethylsilyl)trifluoroacetamide (0.538 ml, 2.0 mmol, BSTFA) was added to a solution of paraherquamide (100 mg, 2.0 mmol) in 5 ml of dry dimethylformamide. The solution was stirred at room temperature for 27 hours then the solvent and excess reagent were evaporated under high vacuum. The residue was dissolved in 4 ml of methanol then 0.4 ml of 2N aqueous hydrochloric acid was added and the solution was immediately cooled to −78° C. Ozone gas in a stream of oxygen was bubbled through the solution at −78° C. for 2 minutes then the solution was allowed to stand at −78° C. for 5 minutes. Methyl sulfide (0.2 ml) was then added and the cold bath removed. The solution was warmed to approximately 5° C. then 5% aqueous NaHCO$_3$ (4 ml) was added and the pH was then adjusted to 10 by addition of 1N aqueous sodium hydroxide. The mixture was extracted with ether (2×3 ml) and dichloromethane (3×3 ml). The combined organic layers were dried with magnesium sulfate, filtered, and evaporated under vacuum. Preparative layer chromatography of the residue on a 2.0 mm silica gel plate eluted with 50% acetone in hexane afforded 77 mg (67%) of a white amorphous solid which was identified by nuclear magnetic resonance and mass spectrometry as 14-O-trimethylsilyl-25-hydroxy-25 hydro-24-nor-paraherquamide.

Selected $^1$H NMR data (300 MHz, CDCl$_3$): 10.66 (1H, br s), 9.22 (1H, br s), 0.18 (9H, TMS).

EXAMPLE 42

14-O-trimethylsilyl 25-fluoro-25-hydro-24-nor-paraherquamide

Diethylaminosulfur trifluoride (0.035 ml, 0.26 mmol, DAST) was added to a cold (0° C.) solution of 14-O-trimethylsilyl-25-hydroxy-25-hydro-24-nor-paraherquamide (60 mg, 0.105 mmol) in 4 ml of chloroform. The solution was stirred at 0° C. for 30 minutes then at room temperature for 1 hour. An additional 0.050 ml of DAST was then added. The red solution was stirred at room temperature for an additional 20 minutes then cooled to 0° C. and 5% NaHCO$_3$ (4 ml) was added. The pH was raised to 10 by careful addition of 1N sodium hydroxide and the layers were separated. The aqueous layer was extracted with dichloromethane (2×3 ml). The combined organic layers were dried with magnesium sulfate, filtered, and evaporated under vacuum. Preparative layer chromatography of the residue on a 1.5 mm silica gel plate eluted with 40% acetone in hexane afforded 46 mg (R$_f$0.42) of 14-O-trimethylsilyl-25-fluoro 25-hydro-24-nor-paraherquamide as a mixture of alpha and beta fluorides. The isomeric fluorides were separated by preparative layer chromatography on a 0.5 mm silica gel plate eluted with ethyl acetate which afforded the 2 pure isomers of 14-O-trimethylsilyl-25-fluoro-25-hydro-24-nor-paraherquamide which were identified by nuclear magnetic resonance and mass spectrometry.

Selected $^1$H NMR data (300 MHz, CDCl$_3$) for the major isomer (22 mg, R$_f$0.55): 9.08 (1H, br s, NH), 6.78 ( (1H, d, J=8 Hz, H$_4$), 6.53 (1H, d, J=8 Hz, H$_5$), 5.65 (1H, d, J=53 Hz, H$_{25}$), 0.16 (9H, s, OTMS). Selected $^1$HNMR data (300 MHz, CDCl$_3$) for the minor isomer (17 mg, R$_f$0.47): 8.14 (1H, br s, NH), 6.79 (1H, d, J=8 Hz, H$_4$), 6.54 (1H, d, J=8 Hz, H$_5$), 5.63 (1H, d, J=53 Hz, H$_{25}$), 0.16 (9H, s, OTMS).

EXAMPLE 43

25-fluoro-25-hydro 24-nor-paraherquamide

A solution of 14-O-trimethylsilyl-25-fluoro-25-hydro-24 nor-paraherquamide (major isomer, 15 mg, 0.026 mmol) in 0.5 ml of a solvent mixture prepared by mixing 2 ml of hydrogen fluoride pyridine complex with 4 ml of pyridine and 14 ml of tetrahydrofuran. The solution was stirred at room temperature for 2.5 hours then diluted with 1 ml of methylene chloride. Aqueous 5% NaHCO$_3$ (1 ml) was then added and the pH adjusted to 10 by careful addition of aqueous 1N sodium hydroxide. The aqueous layer was extracted with methylene chloride (3×2 ml). The combined organic layers were dried with magnesium sulfate, filtered, and evaporated under vacuum. Preparative layer chromatography of the residue on a 0.5 mm silica gel plate eluted with 7% methanol in methylene chloride afforded 11 mg (84%) of a colorless oil (R$_f$0.43) which was identified by nuclear magnetic resonance and mass spectrometry as one isomer of 25-fluoro-25-hydro-24-nor-paraherquamide.

Selected $^1$H NMR data (30 MHz, CDCl$_3$): 8.84 (1H, br s, NH), 6.79 ( (1H, d, J=8 Hz, H$_4$), 6.54 (1H, d, J=8 Hz, H$_5$), 5.66 (1H, d, J=54 Hz, H$_{25}$).

The other isomer of 25-fluoro-25-hydro-24-nor-paraherquamide was obtained by applying the deprotection procedure described above to the minor isomer of 14-O-trimethylsilyl-25-fluoro-25-hydro-24-nor-paraherquamide. The isomer thus obtained (R$_f$ 0.31, isomeric with the compound described above at C-25) was identified by nuclear magnetic resonance and mass spectrometry.

Selected $^1$H NMR data (300 MHz, CDCl$_3$): 7.72 (1H, br s, NH), 6.78 ((1H, d, J=8 Hz, H$_4$), 6.54 (1H, d, J=8 Hz, H$_5$), 5.62 (1H, d, J=54 Hz, H$_{25}$).

EXAMPLE 44

Paraherquamide-2-O-Methyl Imidate

To a 100 mL round bottom flask equipped with a stir bar and containing 2G silica gel (60–200 mesh, dried under vacuum) was added a solution of paraherquamide (100 mg. 0.202 mmol, 1 e.g.) in methylene chloride. The mixture was concentrated to dryness in vacuo. To the silica gel was added 15 mL methylene chloride. The slurry was placed under nitrogen and cooled to 0° C. To the cold slurry was added a 0.25M solution of diazomethane in ether (20 mL., 5 mmol., 25 eq.). The mixture was stirred 2–3h gradually warming to room temperature. The reaction mixture was filtered through a frit to remove silicon dioxide. The silicon dioxide was washed with ethyl acetate. The filtrates were combined and concentrated in vacuo to give a slightly yellow oil. The mixture was separated by preparative TLC (2:1 hexanes/ethyl acetate, 3 elutions) to afford 32 8 mg. paraherquamide 2-O-Methyl imidate characterized by $^1$H NMR, $^{13}$C NMR, and mass spectral analysis.

Selected $^1$H NMR data (300 MHz)(CDCl$_3$) δCHCl$_3$: 2.94 (3H,s,NCH$_3$); 4.06(3H,s,OCH$_3$); 4.82(1H,d,J=7 Hz,H25); 6.43(1H,d,J=7 Hz.,H24); 6.72(1H,d,J=8.5 Hz.,H5); 6.77(1H,d,J=8.5 Hz.,H4) ppm. $^{13}$C NMR (75 MHz)(CDCl$_3$) δCHlC$_3$: 10.6, 21.6, 22.9, 24.3, 26.1, 30.2, 30.5, 36.5, 38.6, 45.9, 52.3, 53.5, 56.9, 59.6, 66.0, 66.6, 71.9, 78.5, 78.9, 115.0, 119.2, 119.7, 133.3, 140.2, 142.3, 143.8, 147.1, 172.3, 184.6 ppm. Mass spectrum (FAB) 508(M$^+$+1).

EXAMPLE 45

14-O-Allyl Paraherquamide-2-O-Methyl Imidate

To a solution of Paraherquamide-2-O-methyl imidate (118 mg, 0.233 mmol., 1 eq.) in dry dimethylformamide (5 ml) in a 25 ml flask was added sodium hydride (56 mg, 1.4 mmol., 6 eq., 60% dispersion in oil) followed by addition of allyl bromide (0.100 mL. 1.165 mmol. 5 eq.). The mixture was stirred at room temperature for 17h. The reaction mixture was poured into a separatory funnel containing saturated aqueous sodium bicarbonate and extracted 4×with methylene chloride. The organic extracts were combined, dried over anhydrous sodium sulfate, filtered, and concentrated in vacuo. The residue was separated by preparative TLC (eluted with 7% methanol/methylene chloride, Rf=0.5) yielding 81.4 mg 14-O-allyl paraherquamide-2O-methyl imidate characterized by $^1$H NMR, $^{13}$C NMR, and mass spectral analysis.

Selected $^1$H NMR data (300 MHz)(CDCl$_3$) δ CHCl$_3$: 4.00–4.15(2H,m,OCH$_2$); 4.09(3H,s,OCH$_3$); 4.83(1H,d,J=8 Hz,H25); 5.09(1H,d,H olefin); 5.50(1H,d,H olefin); 5.89–6.10(1H,m,H olefin); 6.45(1H,d,J=8 Hz,H24); 6.72(1H,d,J=8 Hz,H5); 6.79(1H,d,J=8 Hz,H4) ppm. $^{13}$C NMR (75 MHz)(CDCl$_3$) δ CHCl$_3$: 18.6, 21.9, 22.2, 24.4, 26.2, 30.2, 30.5, 34.4, 36.7, 46.1, 51.9, 53.8, 56.8, 59.9, 63.9, 65.6, 66.6, 72.6, 79.9, 83.6, 115.0, 115.5, 119.3, 119.7, 133.5, 137.0, 140.2, 142.3, 143.8, 147.0, 172.5, 184.7 ppm. Mass spectrum (FAB): 702(M+ +155); 508(M+ +1).

EXAMPLE 46

14-O-Allyl Paraherquamide

To a solution of 14-O-allyl paraherqu amide2-O-methyl imidate (81.4 mg, 0.149 mmol., 1 eq.) in tetrahydrofuran (12 mL) was added 1N; aqueous hydrochloric acid (0.600 mL.). The mixture was stirred at room temperature for 7h, then stored at −4° C. for 15h. The mixture was neutralized with saturated aqueous sodium bicarbonate and the volume was reduced to approx. 3 mL. The reaction mixture was then diluted with saturated aqueous sodium bicarbonate and extracted 4 times with methylene chloride. The organic extracts were combined, dried over anhydrous sodium sulfate, filtered, and concentrated in vacuo. The residue was separated by preparative TLC (eluted with 7% methanol/methylene chloride) to afford 53 mg 14-O-allyl paraherquamide which was characterized by $^1$H NMR, $^{13}$C NMR, and mass spectral analysis.

Selected $^1$H NMR data (300 MHz) (CDCl$_3$) δ CHCl$_3$: 8.14(1H,br s,NH); 6.80 (1H,d,J=8 Hz,H4); 6.66(1H,d,J=8 Hz,H5); 6.11 (1H,d,J=8 Hz,H24); 5.85–6.05(1H,m, H olefin); 5.26(1H,d,H olefin); 5.09(1H,d,H olefin); 4.88 (1H,d,J=8 Hz,H25); 4.0–4.15 (2H,m,OCH$_2$) ppm. $^{13}$C NMR (75 MHz) (CDCl$_3$) δ CHCl$_3$: 18.6, 21.3, 21.9, 24.3, 26.5, 30.3, 30.4, 34.4, 37.8, 47.1, 52.0, 52.3, 60.0, 63.7, 64.0, 65.3, 72.5, 80.9, 83.7, 115.5(2C), 117.7, 120.9, 125.7, 132.9, 135.8, 137.1, 139.5, 146.5, 172.1, 183.3 ppm. Mass spectrum (FAB): 534(M+30 1).

EXAMPLE 47

14-O-Acetyl-Paraherquamide

To a stirred solution of paraherquamide (50 mg., 0.01 mmol., 1 eq.) in nitromethane (1 mL.) at 0° C. was added acetic anhydride (0.02 mL., 2.12 mmol , 21 eq.). To this stirred solution was added a 1M solution of aluminum chloride in nitromethane (0.4 mL., 0.4 mmol., 4 eq.). The mixture was allowed to warm to room temperature over 2 h. The reaction was quenched with excess saturated aqueous sodium bicarbonate and extracted 4 times with methylene chloride. The organic extracts were dried over anhydrous sodium sulfate, filtered and concentrated in vacuo. The product was isolated by preparative TLC on silica (eluted with 2:1 hexanes/ethyl acetate) to give 32 mg. 14-O-acetyl paraherquamide that was characterized by $^1$H NMR, $^{13}$C NMR, and mass spectral analysis.

Selected $^1$H NMR data (300 MHz)(CDCl$_3$) δ CHCl$_3$: 8.19(1H,br s,NH); 6.84(1H,d,J=8 Hz,H4); 6.69(1H,d,J=8 Hz,H5); 6.32(1H,d J=7.5 Hz,H24); 4.89(1H,d,J=7.5 Hz,H25); 3.05(3H,s,NCH$_3$); 2.05(3H,s,COCH$_3$); 1.99(3H,s,CH$_3$) ppm. $^{13}$C NMR (75 MHz)(CDCl$_3$) δ CHCl$_3$: 18.0, 20.5, 22.3, 22.9, 23.7, 25.9, 29.8, 29.9, 33.6, 37.2, 46.5, 51.4, 52.0, 59.2, 63.0, 64.9, 72.0, 79.8, 88.9, 115.1, 117.3, 120.4, 125.0, 132.3, 135.2, 138 9, 146.0, 170.1, 170.3, 182.4 ppm. Mass spectrum (FAB): 536(M+).

EXAMPLE 48

24,25,26,27,28-Penta-Nor-Paraherquamide

To a stirred solution of paraherquamide (20 mg., 0.04 mmol., 1 eq.) in methylene chloride was added thiophenol (0.02 mL., 0.20 mmol., 5 eq.) followed by addition of Boron trifluoride etherate (0.015 mL., 0.12 mmol., 3 eq.). A brown precipitate formed. After 2 h the reaction was quenched by pouring into methanol. The solvent was removed in vacuo. The residue was triturated several times with ether leaving a light tan solid that was characterized by $^1$H NMR, $^{13}$C NMR and mass spectral analysis.

Selected $^1$H NMR data (300 MHz)(CD3OD) δ CH$_3$OH: 6.7(1H,d,J=8.5 Hz,H4); 6.48(1H,d,J=8.5 Hz,H5); 4.01(1H,d,J=12 Hz,H12b); 3.75–3.85(1H,m,H16b); 3.12(3h,s,NCH$_3$); 1.76(3H,s,CH$_3$) ppm. $^{13}$C NMR (75 MHz)(CD3OD) δ CH$_3$OH: 20.4, 20.7, 20.8, 23.6, 27.8, 36.7, 37.9, 46.9, 52.8, 54.1, 57.3, 64.3, 65.6, 77.2, 77.9, 109.8, 118.5, 121.4, 131.2, 131.7, 147.6, 166.9, 184.5 ppm. Mass spectrum (FAB): 428(M+ +1).

EXAMPLE 49

6,7-Di-O-Acetyl-24,25,26,27,28-Penta-Nor-Paraherquamide

To a suspension of penta-nor-paraherquamide (22 mg., 0.05 mmol., 1 eq.) in methylene chloride (1 mL.) was added acetic anhydride (0.014 mL., 0.15 mmol., 3 eq.). Triethylamine (0.021mL., 0.15 mmol., 3 eq.) was added effecting the dissolution of the paraherquamide. A crystal of DMAP was added to the dark solution and the mixture was stirred for 3 h. The mixture was concentrated in vacuo and separated by preparative TLC on silica (eluted with 7% methanol/methylene chloride) to give 5.5 mg. of the diacetate characterized by $^1$H NMR and mass spectral analysis.

Selected $^1$H NMR data (300 MHz)(CDCl$_3$) δ CHCl$_3$: 8.5(1H,br s,NH); 7.07,d,J=8 Hz,H4); 6.84(1H,d,J=8 Hz,H5); 3.05(3H,s,NCH$_3$); 2.32(3H,s,COCH$_3$); 2.31(3H,s,COCH$_3$) PPM. Mass spectrum (FAB): 511(M+).

EXAMPLE 50

6,7-Di-O-Methyl-Penta-Nor-Paraherquamide

To a solution of penta-nor paraherquamide (17 mg., 0.04 mmol., 1 eq.) in methanol (0.5 mL.) was added a 0.28M solution of diazomethane in ether (1.4 mL., 10.3 eq.) A brown precipitate formed. An additional 1 mL. of methanol was added followed by 1.4 mL. of the diazomethane solution. The mixture was stirred for 90 h, diluted with saturated aqueous sodium bicarbonate and extracted 3× with methylene chloride. The organic extracts were combined, dried over anhydrous sodium sulfate, filtered and concentrated in vacuo. The product was isolated by preparative TLC on silica (eluted with 7% methanol/methylene chloride)to afford 2.4 mg. of the dimethyl-penta-nor-paraherquamide that was characterized by $^1$H NMR and mass spectral analysis. Selected $^1$H NMR data (300 MHz)(CDCl$_3$) δ CHCl$_3$: 7.4(1H,br s,NH); 6.86(1H,d,J=8.7 Hz,H4); 6.55(1H,d,J=8.7 Hz,H5); 3.87(6H,s,2×OCH$_3$); 3.07(3H,s,NCH$_3$) ppm. Mass spectrum (FAB): 466 (M$^+$+1).

EXAMPLE 51

5-Nitroparaherquamide

To a suspension of paraherquamide (25 mg., 0.05 mmol., 1 eq.) in methylene chloride (0.25 mL.) at 0° C. was added a solution of 1M nitric acid in ether (0.05 mL., 0.05 mmol., 1 eq.). A 0.5M solution of nitronium tetrafluoroborate in sulfolane (0.20 mL., 0.10 mmol., 2 eq.) was then added dropwise via syringe. The resulting brown mixture was stirred for 75 min. The reaction was diluted with methylene chloride and washed with 5% sodium bicarbonate. The layers were separated and the aqueous layer extracted 3× with methylene chloride. The organic extracts were combined, dried over anhydrous sodium bicarbonate, filtered, and concentrated in vacuo. The product was isolated by preparative TLC on silica (eluted with ethyl acetate) to give 8.4 mg. 5-nitroparaherquamide that was characterized by $^1$H NMR and mass spectral analysis.

Selected $^1$H NMR data (300 MHz)(CDCl$_3$) δ CHCl$_3$: 8.21(1H,br s,NH); 7.48(1H,S,H4); 6.35(1H,d,J=8.5 Hz,H24); 5.07(1H,d,J=8 5 Hz,H25); 3.02(3H,s,NCH$_3$) ppm. Mass spectrum (FAB): 538(M$^+$).

EXAMPLE 52

5-Aminoparaherquamide

To a stirred solution of 5-nitroparaherquamide (29.4 mg., 0.05 mmol., 1 eq.) in acetic acid (1.5 mL.) was added ZnO (125 mg., 1.91mmol., 35 eq.). The mixture was stirred for 6 h. The reaction was quenched by careful addition of saturated aqueous sodium bicarbonate and extracted 4 times with methylene chloride. The organic extracts were combined, dried over anhydrous sodium sulfate, filtered and concentrated in vacuo. The product was isolated by preparative TLC on silica (eluted with 7% methanol/methylene chloride) to give 11 mg. 5-aminoparaherquamide that was characterized by $^1$H NMR and mass spectral analysis.

Selected $^1$H NMR data (300 MHz)(CDCl$_3$) δ CHCl$_3$: 7.40(1H,br s,NH); 6.40(1h,s,H4); 6.30(1H,d,J=8 Hz,H24); 4.88(1H,d,J=8 Hz,H25); 3.05(3H,s,NCH$_3$) ppm. Mass spectrum (FAB): 508(M$^+$).

EXAMPLE 53

5-Acetylaminoparaherquamide

To a stirred solution of 5-aminoparaherquamide (11 mg., 0.02 mmol., 1 eq.) in methylene chloride (0.5 mL.) was added acetic anhydride (0.006 mL., 0.06 mmol., 3 eq.) followed by addition of triethylamine ( 0.009 mL., 0.06 mmol., 3 eq.). To the reaction mixture was added a small crystal of dimethylaminopyridine. The mixture was stirred 2 h. The product was isolated directly by preparative TLC on silica (eluted with 1:1 hexanes ethyl acetate) to give 9.6 mg. 5-acetylaminoparaherquamide that was characterized by $^1$H NMR and mass spectral analysis. Mass spectrum (FAB): 551(M$^+$+1).

EXAMPLE 54

14-O-Methylparaherquamide-2-O-Methyl Imidate

To a stirred solution of paraherquamide 2-O-methyl imidate (16.9 mg., 0.033 mmol., 1 eq.) in dry tetrahydrofuran (0.75 mL.) was added sodium hydride (11.5 mg., 0.288 mmol., 8 eq., 60% dispersion in oil). After 5 min a 1M solution of methyl iodide (0.100 mL., 0.100 mmol., 3 eq.) was added. The mixture was stirred 18 h, then quenched with saturated aqueous sodium bicarbonate and extracted 4 times with methylene chloride. The organic extracts were combined, dried over anhydrous sodium sulfate, filtered and concentrated in vacuo. The product was isolated by preparative TLC on silica (eluted with 7% methanol/methylene chloride) to give 12.4 mg. 14-Omethyl paraherquamide 2-O-methyl imidate characterized by $^1$H NMR, and mass spectral analysis.

Selected $^1$H NMR data (300 MHz)(CDCl$_3$) δ CHCl$_3$: 6.79(1H,d,J=8 Hz,H4); 6.75(1H,d,J=8 Hz,H5); 6.47(1H,d,J=8 Hz,H24); 4.85(1H,d,J=8 Hz,H25); 4.09(3H,s,OCH$_3$); 3.27(3H,s,OCH$_3$); 2.90(3H,s,NCH$_3$) ppm. Mass spectrum (FAB): 522(M$^+$+1).

EXAMPLE 55

14-O-Methyl Paraherquamide

To a stirred solution of 14-O-methyl paraherquamide 2-O-methyl imidate (23.8 mg., 0.045 mmol., 1 eq.) in tetrahydrofuran (2 mL ) was added 1N hydrochloric acid (0.180 mL., 0.180 mmol., 4 eq.). The mixture was stirred 1h, then diluted with saturated aqueous sodium bicarbonate and extracted 4× with methylene chloride. The organic extracts were combined, dried over anhydrous sodium bicarbonate filtered, and concentrated in vacuo. The product was isolated by preparative TLC on silica (eluted with 7% methanol/methylene chloride) to afford 14.2 mg. 14-O-methyl paraherquamide characterized by $^1$H NMR, and mass spectral analysis.

Selected $^1$H NMR data (300 MHz)(CDCl$_3$) δ CHCl$_3$: 7.5(1H,br s,NH); 6.80(1H,d,J=8 Hz,H24); 6.68(1H,d,J=8 Hz,H5); 6.30(1H,d,J=8 Hz,H24); 4.89(1H,d,J=8 Hz,H25); 3.27(3H,s,OCH$_3$); 3.06(3H,s,NCH$_3$) ppm. Mass spectrum (FAB): 508(M$^+$+1).

EXAMPLE 56

14O-Benzyl Paraherquamide 2-O-Methyl Imidate

A solution of paraherquamide 2-O-methyl imidate (27 mg., 0.053 mmol., 1 eq.), sodium hydride (11.9 mg., 0.298 mmol., 5.6 eq., 60% dispersion in oil) and benzyl bromide (0.025 mL., 0.216 mmol., 4 eq.) in dry dimethylformamide (0.5 mL.) was treated as described in Example 45 furnishing 14.4 mg. 14-O-benzyl paraherquamide 2-O-methyl imidate characterized by $^1$H NMR and mass spectral analysis.

Selected $^1$H NMR data (300 MHz)(CDCl$_3$) δ CHCl$_3$: 7.2-7.4 5H,m); 6.81(1H,d,J=8 Hz,H4); 6.75(1H,d,J=8 Hz,H5); 6.48(1H,d,J=7.5 Hz,H24); 4.86(1H,d,J=7.5 Hz,H25); 4.65(2H,ABq,J=12.5 Hz,OCH$_2$); 4.11(3H,s,OCH$_3$); 3.00(3H,s,NCH$_3$) ppm. Mass spectrum (FAB): 598(M$^+$+1).

EXAMPLE 57-A

14-O-Benzyl Paraherquamide

A solution of 14-O-benzyl paraherquamide 2-O-methyl imidate (14.4 mg., 0.024 mmol., 1 eq.) and 1N hydrochloric acid (0.100 mL., 0.100 mmol., 4 eq.) in tetrahydrofuran (2 mL.) was treated as described in Example 55 to afford 9.5 mg. 14-O-benzyl paraherquamide characterized by $^1$H NMR and mass spectral analysis.

Selected $^1$H NMR data (300 MHz)(CDCl$_3$) δ CHCl$_3$: 7.45(1H,br s,NH); 7.2-7.4(5H,m); 6.82(1H,d,J=8.5 Hz,H4); 6.68(1H,d,J=8.5 Hz,H5); 6.30(1H,d,J=8 Hz,H24); 4.8.(1H,d,J=8 Hz,H25); 4.65(2H ABq,J=12.5 Hz,OCH$_2$); 3.06(3H,s,NCH$_3$) ppm. Mass spectrum (FAB): 584(M$^+$+1).

EXAMPLE 57-B

14-O-Ethyl Paraherquamide 2-O-Methyl Imidate

A solution of paraherquamide 2-O-methyl imidate (26.8 mg., 0.053 mmol., 1 eq.), sodium hydride (15.2 mg., 0.380 mmol., 7.2 eq., 60% dispersion in oil), and ethyl iodide (0.030 mL., 0.290 mmol., 5.5 eq.) in dry dimethylformamide (1 mL.) was treated as described in Example 45 to afford 11.4 mg. 14-O-ethyl paraherquamide 2-O-methyl imidate characterized by $^1$H NMR analysis.

Selected 1H NMR data (300 MHz)(CDCl$_3$) δ CHCl$_3$: 6.79(1H,d,J=8 Hz,H4); 6.74(1H,d,J=8 Hz,H5); 6.48(1H,d,J=8.5 Hz,H24); 4.85(1H,d,J=8.5 Hz,H25); 4.10(3H,s,OCH$_3$); 3.49-3.61(3H,M,H12b and OCH$_2$); 2.97(3H,s,NCH$_3$) ppm.

EXAMPLE 58

14-O-Ethyl Paraherquamide

A solution of 14-O-ethyl paraherquamide 2-O-methyl imidate (11.4 mg., 0.021 mmol., 1 eq.) and 1N hydrochloric acid (0.085 mL., 0.085 mmol., 4 eq.) in tetrahydrofuran (1.5 mL.) was treated as described in Example 45 furnishing 8.2 mg. 14-O-ethyl paraherquamide characterized by 1H NMR and mass spectral analysis.

Selected 1H NMR data (300 MHz)(CDCl$_3$) δ CHCl$_3$: 7.59(1H,br s,NH); 6.81(1H,d,J=8 Hz,H4); 6.67(1H,d,J=8 Hz,H5); 6.31(1H,d,J=8 Hz,H24); 4.89(1H,d,J=8 Hz,H25); 3.5-3.6(3H,m,H12b and OCH$_2$); 3.04(3H,s,NCH$_3$) ppm. Mass spectrum (FAB): 522(M$^+$+1).

EXAMPLE 59

14-O-(2-Methoxyethoxy)methyl Paraherquamide

To a stirred solution of paraherquamide 2-O-methyl imidate (29.3 mg., 0.058 mmol., 1 eq.) in dry dimethylformamide (1 mL.) under nitrogen was added sodium hydride (12.8 mg., 0.320 mmol., 5.5 eq., 60% dispersion in oil) followed by addition of MEM-Cl (0.033 mL., 0.289 mmol., 5 eq.). After stirring 4 h additional portions of sodium hydride (11 mg.) and MEM-Cl (0.033 mL.) were added. The mixture was stirred 14.5 h The reaction was quenched with excess saturated aqueous sodium bicarbonate and extracted 4× with methylene chloride. The organic extracts were combined, dried over anhydrous sodium sulfate, filtered, and concentrated in vacuo. The product was isolated by preparative TLC on silica (eluted with 7% methanol/methylene chloride) to afford 11.5 mg. 14-O-(2 methoxyethoxy)methyl paraherquamide characterized by $^1$H NMR and mass spectral analysis.

Selected $^1$H NMR data (300 MHz)(CDCl$_3$) δ CHCl$_3$: 7.59(1H,br s,NH); 6.79(1H,d,J=8 Hz,H4); 6.66(1H,d,J=8 Hz,H5); 6.29(1H,d,J=8 Hz,H24); 4.95(1H,d,J=8 Hz,OCH$_2$O); 4.87(2H,d,J=8 Hz,H25 and OCH$_2$O); 3.37(3H,s,OCH$_3$); 3.03(3H,s,NCH$_3$) ppm. Mass spectrum (FAB): 582(M$^+$+1).

EXAMPLE 60

14-O-(Methoxy)methyl Paraherquamide 2-O-Methyl Imidate

A solution of paraherquamide 2-O-methyl imidate (33.9 mg., 0.067 mmol., 1 eq.), sodium hydride (12.8 mg., 0.320 mmol., 4.8 eq., 60% dispersion in oil), and chloromethyl methyl ether (0.025 mL., 0.329 mmol., 4.9 eq.) was treated as described in Example 54 to give 7.8 mg. 14-O-(methoxy)methyl paraherquamide 2-O-methyl imidate characterized by $^1$H NMR analysis.

Selected $^1$H NMR data (300 MHz)(CDCl$_3$) δ CHCl$_3$: 6.78(1H,d,J=8.5 Hz,H4); 6.72(1H,d,J=8.5 Hz,H5); 6.46(1H,d,J=8 Hz,H24); 4.87(1H,d,J=8 Hz,OCH$_2$O); 4.84(1H,d,J=8 Hz,H25); 4.77(1H,d,J=8 Hz,OCH$_2$O); 4.09(3H,s,OCH$_3$); 3.37(3H,s,OCH$_3$); 2.97(3H,s,NCH$_3$) ppm.

EXAMPLE 61

14-O-(METHOXY)METHYL PARAHERQUAMIDE

A solution of 14-O-(methoxy)methyl paraherquamide 2-O-methyl imidate (7.8 mg., 0.014 mmol., 1 eq.) and 1N hydrochloric acid (0.057 mL., 0.057 mmol., 4 eq.) in tetrahydrofuran (0.5 mL.) was treated as described in Example 55 to afford 3.8 mg. 14-O-(methoxy)methyl paraherquamide characterized by $^1$H NMR and mass spectral analysis.

Selected $^1$H NMR data (300 MHz)(CDCl$_3$) δ CHCl$_3$: 7.45(1H,br s,NH); 6.79(1H,d,J=8 Hz,H4); 6.66(1H,d,J=8 Hz,H5); 6.29(1H,d,J=7.5 Hz,H24); 4.87(2H,d,J=8 Hz,H25 and OCH$_2$O); 4.76(1H,d,J=8 Hz,OCH$_2$O); 3.36(3H,s,OCH$_3$); 3.02(3H,s,NCH$_3$) ppm. Mass spectrum (FAB): 538(M$^+$+1).

EXAMPLE 62

14-O-(N,N'-Dimethylureido)carbonyl Paraherquamide 2-O-Methyl Imidate

A solution of paraherquamide 2-O-methyl imidate (30 mg., 0.059 mmol., 1 eq.), sodium hydride (35 mg., 0.885 mmol., 15 eq.) and methyl isocyanate (0.012 mL., 0.708 mmol., 12 eq.) in dry tetrahydro furan ( 0.2 mL.) was treated as described in Example 54 furnishing 14-O-(N,N'-dimethylureido)carbonyl paraherquamide 2-O-methyl imidate characterized by $^1$H NMR analysis.

Selected $^1$H NMR data (300 MHz)(CDCl$_3$) δ CHCl$_3$: 6.78(1H,d,J=8 Hz,H4); 6.72(1H,d,J=8 Hz,H5); 6.45(1H,d,J=7.5 Hz,H24); 4.48(1H,d,J=7.5 Hz,H25); 4.09(3H,s,OCH$_3$); 3.21(3H,s,NCH$_3$); 2.98(3H,s,NCH$_3$); 2.83(3h,d,NCH$_3$) ppm.

EXAMPLE 63

14-O-(N,N'-Dimethylureido)carbonyl Paraherquamide

A solution of 14-O-(N,N'-dimethylureido)carbonyl paraherquamide 2-O-methyl imidate (15.5 mg., 0.027 mmol., 1 eq.) and 1N hydrochloric acid (0.110 mL, 0.110 mmol., 4 eq.) in tetrahydrofuran (1 mL.) was treated as described in Example 55 to afford 9.4 mg. 14-O-(N,N'dimethylureido)carbonyl paraherquamide characterized by $^1$H NMR and mass spectral analysis. Selected $^1$H NMR data (300 MHz)(CDCl$_3$) δ CHCl$_3$: 8.45(1H,br s,NH); 7.60(1H,br s,NH); 6.80(1H,d,J=8.5 Hz,H4); 6.67(1H,d,J=8.5 Hz,H5): 5.29(1H d,J=8 Hz,H24): 4.88(1H,d,J=8 Hz,H25); 3.22(3H,s,NCH$_3$); 3.03(3H,s,NCH$_3$); 2.83(3H,d,NCH$_3$) ppm. Mass spectrum (FAB): 608(M+ +1).

EXAMPLE 64

14-O-Butyl Paraherquamide 2-O-Methyl Imidate

A solution of paraherquamide 2-O-methyl imidate (34.1 mg., 0.067 mmol., 1 eq.), sodium hydride (13.7 mg., 0.348 mmol., 5.1 eq.) and n-butyl iodide (0.060 mL., 0.538 mmol., 8 eq.) in dry dimethylformamide (1 mL.) was treated as described in Example 45 to afford 7.1 mg. 14-O-butyl paraherquamide 2-O-methyl imidate characterized by $^1$H NMR analysis.

Selected $^1$H NMR data (300 MHz)(CDCl$_3$) δ CHCl$_3$: 6.78(1H,d,J=8 Hz,H4); 6.72(1H,d,J=8 Hz,H5); 6.46(1H,d,J=7.5 Hz,H24); 4.84(1H,d,J=7.5 Hz,H25); 4.09(3H,s,OCH$_3$); 3.35-3.50(2H,m,OCH$_2$); 2.95(3H,s,NCH$_3$) ppm.

EXAMPLE 65

14-O-Butyl Paraherquamide

A solution of 14-O-butyl paraherquamide 2-O-methyl imidate (5.7 mg., 0.010 mmol., 1 eq.) and 1N hydrochloric acid (0.040 mL., 0.040 mmol., 4 eq.) in tetrahydrofuran (0.5 mL.) was treated as described in Example 55 to furnish 3.3 mg. 14-O-butyl paraherquamide characterized by $^1$H NMR and mass spectral analysis.

Selected $^1$H NMR data (300 MHz)(CDCl$_3$) δ CHCl$_3$: 7.6(1H,br s,NH); 6.79(1H,d,J=8.5 Hz,H4); 6.65(1H,d,J=8.5 Hz,H5); 6.29(1H,d,J=7.5 Hz,H24); 4.85(1H,d,J=7.5 Hz,H25); 3.35-3.50(2H,-m,OCH$_2$);3.01(3H,s,NCH$_3$) ppm. Mass spectrum (FAB): 704(M+ +155); 550(M+ +1).

EXAMPLE 66

14-O-Propargyl Paraherquamide 2-O-Methyl Imidate

A solution of paraherquamide 2-O methyl imidate (24.6 mg., 0.048 mmol., 1 eq.), sodium hydride (12 mg., 0.300 mmol., 6.2 eq., 60% dispersion in oil), and 80% propargyl bromide in toluene (0.045 mL., 0.404 mmol., 8.3 eq.) in dry dimethylformamide was treated as described in Example 45 yielding 3.0 mq. 14-O-propargyl paraherquamide 2-O-methyl imidate characterized by $^1$H NMR analysis.

Selected $^1$H NMR data (300 MHz)(CDCl$_3$) δ CHCl$_3$: 6.78(1H,d,J=8.5 Hz,H4); 6.73(1H,d,J=8.5 Hz,H5); 6.46(1H,d,J=7.5 Hz,H24); 4.84(1H,d,J=7.5 Hz,H25); 4.35(1H,dd,J=2 Hz,J=12 Hz,OCH$_2$); 4.22(1H,dd,J=2Hz,J=15 Hz,OCH$_2$); 4.09(3H,s,OCH$_3$); 2.95(3H,s,NCH$_3$) ppm.

EXAMPLE 67

14-O-Propargyl Paraherquamide

A solution of 14-O-propargyl paraherquamide 2-O-methyl imidate (6.9 mg., 0.012 mmol., 1 eq.) and 1N hydrochloric acid (0.050 mL., 0.050 mmol., 4 eq.) in tetrahydrofuran (0.5 mL.) was treated as described in Example 55 furnishing 2.8 mg. 14-O-propargyl paraherquamide characterized by $^1$H NMR and mass spectral analysis.

Selected $^1$H NMR data (300 MHz)(CDCl$_3$) δ CHCl$_3$: 7.43(1H,br s,NH); 6.79(1H,d,J=8 Hz,H4); 6.65(1H,d,J=8 Hz,H5); 6.29(1H,d,J=7.5 Hz,H24); 4.87(1H,d,J=7.5 Hz,H25); 4.34(1H,br d,OCH$_2$); 4.11(1H,br d,OCH$_2$); 3.01(3H,s,NCH$_3$) ppm. Mass spectrum (FAB): 686(M+ +155); 532(M+ +1).

EXAMPLE 68

6-O-Allyl-24,25,26,27,28-Penta-Nor Paraherquamide

To a stirred solution of penta-nor paraherquamide (17 mg., 0.04 mmol., 1 eq.) in dry dimethylformamide (0.5mL.) was added sodium hydride (3.2 mg., 0.08 mmol., 2 eq., 60 % dispersion in oil) followed by addition of allyl bromide (0.007 mL., 0.08 mmol., 2 eq.). The mixture was allowed to stir overnight under nitrogen. The mixture was concentrated in vacuo, diluted with saturated aqueous sodium bicarbonate and extracted 5 times with methylene chloride. The organic extracts were combined, dried over anhydrous sodium sulfate, filtered, and concentrated in vacuo. The product was isolated by preparative TLC on silica (eluted with 7 methanol/methylene chloride) to afford 6-O-allyl-24,25,26,27,28-pentanor-paraherquamide characterized by $^1$H NMR and mass spectral analysis.

Selected $^1$H NMR data (300 MHz)(CD3OD) δ CH$_3$OH: 6.86(1H,d,J=7.5 Hz,H4); 6.49(1H,d,J=7.5 Hz,H5); 6.02-6.18(1H,m,H olefin); 5.13-5.28(2H,m,H olefin); 4.51(2H,d,OCH$_2$); 3.03(3H,s,NCH$_3$) ppm. Mass spectrum (FAB): 622(M+ +155); 468(M+ +1).

STARTING MATERIAL PREPARATION

EXAMPLE P-1

A 5% portion of an 18×150 MM test tube containing 3.5 g of soil and dried culture MF 5123 (ATCC 20841) was used to inoculate an unbaffled Erlenmeyer flask containing 50 ml of Medium 1. After three days of incubation of 28° C., agitated on a rotary shaker (5 cm throw) at 212 rpm, a 2.0 ml aliquot of the growth was aseptically transferred to a 250 ml Erlenmeyer flask containing Medium 2. After inoculation, Medium 2 was incubated 7 days without agitation at 25° C. After 7 days of incubation 15 ml of sterile distilled water was added to each flask. Incubation was then continued at 25° C. for a further seven days with agitation on a rotary shaker at 160 rpm.

EXAMPLE P-2

A 2.0 ml volume of a frozen vegetative qrowth in 10% glycerol of the culture MF 5123 (ATCC 20841) was used to inoculate an unbaffled Erlenmeyer flask containing 50 ml of Medium 1. After 3 days of incubation at 28° C., agitated on a rotary shaker (5 cm throw) at 212 rpm, a 2.0 ml portion of the growth was aseptically transferred to a 250 ml Erlenmeyer flask containing Medium 2. After inoculation, Medium 2 was incubated 7 days without agitation at 25° C. After 7 days of incubation 15 ml of sterile distilled water was added to each flask. Incubation was then continued at 25° C. for a further 9 days with agitation on a rotary shaker at 160 rpm.

EXAMPLE P-3

A 2.0 ml volume of a frozen vegetative growth in 10% glycerol of the culture MF 5123 (ATCC 20841) was used to inoculate an unbaffled Erlenmeyer flask containing 50 ml of Medium 1. After 3 days of incubation at 28° C., agitated on a rotary shaker (5 cm throw) at 212 rpm, a 2.0 ml portion of the growth was aseptically transferred to a 250 ml Erlenmeyer flask containing Medium 2. After inoculation, Medium was incubated for 7 days without agitation at 25° C.

| Medium 1 | |
|---|---|
| Corn Steep Liquor | 5.0 g |
| Tomato Paste | 40.0 g |
| Oat Flour | 10.0 g |
| Glucose | 10.0 g |
| Trace Elements Mix | 10.0 ml |
| Distilled Water | q.s. 1000 ml |
| pH 6.8 | |
| Trace Elements Mix | |
| $FeSO_4.7H_2O$ | 1.0 g |
| $MnSO_4.4H_2O$ | 1.0 g |
| $CuCl_2.2H_2O$ | 25.0 mg |
| $CaCl_2$ | 0.1 g |
| $(NH_4)_6MoO_2.4H_2O$ | 19.0 mg |
| $ZnSO_4.7H_2O$ | 0.2 g |
| Distilled Water | q.s. 1000 ml |

| Medium 2 | |
|---|---|
| Amount per 250 ml Erlenmeyer flask | |
| Corn | 10.0 g |
| Yeast extract | 0.5 g |
| Sodium tartrate | 0.1 g |
| $FeSO_4.7H_2O$ | 0.01 g |
| L-cysteine | 0.1 g |
| Glycerol | 0.5 ml |
| $CoCl_2.6H_2O$ | 0.002 g |
| Distilled Water | 15.0 ml |
| Autoclave | 20 minutes, 15 pounds, 121° C. |
| then Distilled Water | 10.0 ml |
| re-autoclave | 20 minutes, 15 pounds, 121° C. |

EXAMPLE P-4

The contents of six seven day solid media 250 ML fermentation flasks from Example 3 were combined and extracted twice with six hundred ml. of ethyl acetate. The extracts were combined, dried with sodium sulfate and concentrated to 60 ml.

A three ml. aliquot of the 60 ml concentrate was further concentrated to 0.5 ml. This sample was subjected to preparative thin layer chromatography on an E. Merck Silica-Gel 60 (0.5 mm thickness) plate using a solvent system of 5:5:0.5 v/v/v hexane:methylene chloride:methanol. After chromatography nine zones were selected by U.V. quenching and iodine staining of a template section of the plate. The selected areas were scraped and each eluted with 2 ml. of methanol. The eluted samples were labeled A thru I. One hundred mcl of each sample was submitted for C. elegans assay. Sample C Rf=0.16 was active against C. elegans. Sample C was concentrated to dryness and the residue taken up in 400 mcl of methanol and subjected to preparative HPLC chromatography on a DuPont Zorbax ODS 0.94×25 cm column maintained at 60 degrees C. The chromatography was carried out using an isocratic system of 65:35 v/v methanol:water at a flow rate of 4 ml/min. for thirty minutes followed by a linear gradient to 100% methanol over 10 minutes and held at 100% methanol for 35 minutes. The effluent stream was monitored at 226 nm and a setting of 1.28 AUFS using a Laboratory Data Control SpectroMonitor II detector equipped with a 1 mm path length cell, and a Spectra-Physics SP4100 Computing Integrator. Twenty five fractions were collected. Fraction nine with a retention time of 11.3 minutes was active against C. elegans. Fractions eight thru twelve were combined and concentrated to dryness. The residue was labeled J and submitted for N.M.R. and mass spectral analysis and identified as structure I Paraherquamide. Sample J contained 1.8 mg. of paraherquamide based on U.V. analysis using published U.V. data (Tetrahedron Letters Vol. 22 pp 135–136 1980).

EXAMPLE P-5

The contents of sixteen-seven day solid media 250 ml fermentation flasks from Example P-3 were combined and extracted with three one liter portions of ethyl acetate. High pressure liquid chromatography (HPLC) analysis of the three extracts indicated that extracts one and two contained 430 and 130 mg respectively of paraherquamide. Extract three contained only 4 mg and was discarded. Extracts one and two were combined and dried with sodium sulfate. The dried extract was concentrated to an oily residue. The residue was taken up in methanol to a volume of 40 ml. This solution was chromatographed on a 200 ml column of LH-20, previously equilibrated with methanol, using methanol at a flow rate of 3 ml./min collecting a 40 ml fore cut followed by sixty-one seven ml fractions. HPLC analysis showed that fractions 10 thru 16 contained paraherquamide Rt=7.9 minutes. Fractions 10 thru 16 were combined and concentrated to an oily residue. The residue was taken up in 5:5:0.5 v/v/v hexane:methylene chloride:methanol to a volume of 13.5 ml. This solution was chromatographed on a 500 ml column of E. Merck Silica-Gel 60 (0.04 to 0.063 mm particle size) previously equilibrated with the same solvent system at a flow rate of 10 ml/min. A 200 ml forecut was collected followed by 315 eight ml fractions. Fractions were combined as follows based on T.L.C. analysis. Fractions 150 to 179; 180 to 199; 200 to 239; 240 to 270; and 271 to 315. The combined fractions were labeled A thru E. Samples C and D were combined, concentrated to dryness and labeled F. Sample F was taken up in 2 ml of methanol and filtered. The filtrate was subjected to preparative HPLC chromatography using a Whatman Magnum 20 ODS-3 2.2×25 cm column at room temperature using an isocratic solvent system of 68/32 v/v methanol/water at a flow of 10 ml/min. The effluent stream was monitored using a Gilson model 116 U.V. detector equipped with a 0.05 mm path length cell and a setting of 1.28 AUFS, the detector signal being monitored by a Spectra-Physics SP4100 Computing Integrator. Thirty fractions were collected. Fractions 16 thru 18 were combined, based on the U.V. recording. The combined fractions were concentrated to dryness to yield 205.4 mg of pure paraherquamide, structure I.

EXAMPLE P-6

Solid Phase Fermentation. The inoculant was prepared by placing the contents of one frozen vial of MF-5123 (ATCC 20841) into 54 ml of medium 1 in a 250 ml flask and agitated at 28° C. for 48 hours on a rotary shaker at 220 rpm. At the completion of the fermentation period 10 ml of the fermentation broth was transferred to 800 ml of medium 1 in a 2 liter flask and agitated at 28° C. for 48 hours on a rotary shaker at 200 rpm.

The production medium was prepared by dissolving all of the ingredients of medium 3 except the cracked corn in 3.5 l of distilled water and combining this solution with 3 kg of cracked corn in a 50×75×5 cm filter tray. The tray was sterilized uncovered for 20 minutes at 121° C. The contents of the tray were stirred and another tray of the same dimension was placed over the first as a lid and taped tightly closed. The covered tray was autoclaved for an additional 20 minutes at 121° C. The tray was removed from the autoclave and allowed to cool for several hours before inoculation. After cooling, the tray was inoculated with 1 liter of the inoculant. The inoculant was distributed uniformly throughout the medium by mixing with a sterile spatula. The lid was taped securely to the tray and the solid culture fermented at 25° C. for several days without agitation.

The above solid phase fermentation was repeated using the same procedure with the exception that after the uncovered sterilization 2.0 liter of distilled water was added to the tray.

| Medium 3 (Solid phase production medium) | |
|---|---|
| Material | concentration (g/tray) |
| Cracked corn (Agway) | 3000.0 |
| Yeast extract | 150.0 |
| Sodium tartrate | 30.0 |
| $FeSO_4.7H_2O$ | 3.0 |
| $CoCl_2.6H_2O$ | 0.6 |
| L-cysteine | 30.0 |
| Glycerol | 150.0 |
| pH - No adjustment | |

EXAMPLE P-7

A tray of 3 kg of solid media from Example P-6 and 20 flasks containing 80 gm of solid media (2) each from Example 3 were extracted with ethyl acetate using 2×600 ml of solvent per flask and 2×4 liters of solvent per tray. The extracts were combined, labeled A and stored at 5° C. A tray of 3 kg solid media (2) and 20 flasks containing 80 gm of solid media per flask were extracted with ethyl acetate and the extracts combined and labeled B.

Samples A and B were combined and concentrated, under reduced pressure at 26° C., to 800 ml. This concentrate was further concentrated, using high vacuum and a 40° C. water bath, to a volume of 300 ml. Three hundred ml of methanol was added to the oily concentrate. Precipitation was observed and the solution was stored at 5° C. overnight. The precipitate was removed by filtration and washed with 200 ml of methanol. The filtrate and the methanol wash were combined giving a volume of 800 ml which was labeled C. HPLC analysis of Sample C indicated the presence of 4.3 gm of paraherquamide. Sample C was concentrated under reduced pressure, to remove methanol to a final volume of 200 ml. To this concentrate 200 ml of acetonitrile was added and labeled D. Solution D was extracted with 1×400 ml of hexane followed by 3×300 ml hexane extractions. The acetonitrile layer, 310 ml, contained 3.9 gm of paraherquamide, by HPLC analysis. The acetonitrile solution was concentrated to dryness and labeled E. The hexane extracts were discarded.

EXAMPLE P-8

Sample E from Example P-7 was taken up in 1:1 methylene chloride/ethyl acetate to a volume of 180 ml. The solution was chromatographed on a 4 liter column of silica gel (Grace), which had previously been equilibrated with ethyl acetate. The chromatography was carried out with ethyl acetate at a flow rate of 200 ml/min collecting five four liter fractions followed by 24×500 ml fractions. Fractions 3 thru 9 containing 1.95 gms of paraherquamide were combined and labeled F. Fraction two, which was highly colored and contained considerable paraherquamide, was concentrated to dryness for rechromatography. The residue, which was labeled G, was taken up in 1:1 methylene chloride: ethylacetate to a volume of 180 ml and chromatographed as above. Five four liter fractions followed by 24×500 ml fractions were collected. Fractions 4 thru 17 containing paraherquamide were combined and labeled H. Samples F and H were combined. HPLC analysis of the combined fractions indicated they contained 4 gms of paraherquamide. The combined sample was concentrated to yield 9.5 grams of solids which were labeled J.

EXAMPLE P-9

Sample J from Example P-8 was taken up in 3:1 methanol:methylene chloride to a volume of 110 ml and applied to a 2"×6' Sephadex LH 20 column previously equilibrated with methanol. Chromatography was carried out with methanol at a flow rate of 20 ml/min collecting 20 ml fractions. The fractions were analyzed by T.L.C. and HPLC and paraherquamide was found to be present in fractions 155 thru 186. Fractions 155 thru 164 combined and labeled A. Fractions 165 thru 175 combined and labeled B. Fractions 176 thru 186 combined and labeled C. Samples A and B were each concentrated to dryness and their residue triturated with 20 ml of cold ethyl acetate. The triturates were filtered and the solids combined and labeled D. The filtrates were combined and labeled E.

EXAMPLE P-10

Sample D from Example P-9 was taken up in 80 ml of 2:1 hexane:acetone and chromatographed, in two 40 ml portions, on silica gel (Grace) previously equilibrated with 2:1 hexane acetone. Portion one was chromatographed on one liter of silica gel and portion two on 700 ml of silica gel. Chromatography in both instances was carried out with 2:1 hexane:acetone at a flow rate of 20 ml/min collecting 25 ml fractions. Fractions 153 thru 220 and 143 thru 230 from the respective columns contained a total of 3.5 gms of paraherquamide.

EXAMPLE P-11

Paraherquamide (5 mg, 0.01 moles) was dissolved in 2 mL of methanol. 10% palladium-on-carbon (5 mg) was added and hydrogenation carried out under 40 psig, 23° C. for 2.5 hours. Reaction was 100% completed after 2.5 hours and no side products were observed as determined by HPLC and TLC. The reaction mixture was filtered and the catalyst washed with methanol. The combined methanol solutions containing dihydroparaherquamide were taken to dryness and purified initially by HPLC on an analytical Whatman ODS-3 column using a 60:40, water:methanol 1% acetic acid and 0.1% triethylamine solvent system delivered at 1.5 mL/min. A 40% aqueous methanol solvent system was used subsequently for final purification. Identification was based on mass spectral and NMR analyses.

What is claimed is:

1. A compound having the formula:

[Chemical structure showing a polycyclic compound with labels $R_5$, 6, Y, 7, 8, $H_3C$, $CH_3$, $R_{12}$, 3Z, N, X, 13, N, 29, O, $CH_3$]

wherein:

X = [Substructure A: five-membered ring with $R_{16}$, N-13, OR, $R_{14a}$, $R_{14b}$]  OR  [Substructure B: ring with O, carbonyl, N-13, OR, $H_3C$, $R_{30}$]

(Substructure A)    (Substructure B)

[Substructure C: HO, $R_N$, N-13, $H_3C$, $R_{30}$]

(Substructure C)

Y = [Substructure D: $H_3C$, $CH_3$, O, 6, 7, O, $R_{25}$, $R_{24}$]  OR  [Substructure E: $R_{26}$, $R_{26}$, O, 6, $R_{24}$, 7, O]

(Substructure D)    (Substructure E)

[Substructure F: 6-$OR_6$, 7-$OR_7$]

(Substructure F)

Z = [Substructure G: 8, 3, N, $R_1$, O]  OR  [Substructure H: 8, 3, N, $OR_2$]

(Substructure G)    (Substructure H)

$R_1$ is hydrogen, loweralkyl, lower alkanoyl, or substituted benzenesulfonyl;
$R_2$ is loweralkyl;
$R_5$ is hydrogen, halogen, amino, nitro, or loweralkanoylamino;
$R_6$ is hydrogen, loweralkyl or lower alkanoyl;
$R_7$ is hydrogen, loweralkyl or lower alkanoyl;
$R_{12}$ is hydrogen or $R_{12}$ can also be oxo provided that $R_{16}$ is hydrogen;
$R_{14a}$ is hydrogen, hydroxy, lower alkoxy, lower alkenylloweralkoxy, lower alkynylloweralkoxy, lower alkanoyloxy, polyalkoxyalkoxy, phenyl, lower alkyl, triloweralkylsilyloxy, diphenylphosphoryloxy, or halogen;
$R_{14b}$ is hydrogen, hdyroxy, lower alkyl, lower alkenyl, phenyl, phenylloweralkyl, lower alkoxy or lower alkanoyloxy;
$R_{16}$ is hydrogen or $R_{16}$ can be oxo provided that $R_{12}$ is hydrogen;
$R_{24}$ is hydrogen, halogen, hydroxy, loweralkoxy, loweralkanoyloxy, or triloweralkylsilyloxy;
$R_{25}$ is hydrogen or halogen;
$R_{26}$ is hydrogen or methyl;
$R_{30}$ is hydrogen, halogen, hydroxy, loweralkoxy, loweralkanoyloxy, hydrazono, semicarbazono;
$R_N$ is hydrogen or lower alkyl; and the broken line represents a single or double bond between carbons 24 and 25; provided that the various R groups are not such that the compounds paraherquamide, 24,25-dihydroparaherquamide, 14-deoxyparaherquamide, and 14-deoxy-14-dimethyl-paraherquamide are defined and the term substitutetd benzenesulfonyl is defined as mono, di, or trilower alkoxy-benzenesulfonyl, or mono, di, or tri-halo-benzenesulfonyl.

2. The compound of claim 1 wherein
X is substructure B
Y is substructure D
Z is substucture G
$R_1$ is hydrogen, loweralkyl, lower alkanoyl, or substituted benzenesulfonyl;
$R_5$ is hydrogen, halogen, amino, nitro, or loweralkanoylamino;
$R_{24}$ is hydrogen, halogen, hydroxy, loweralkoxy, loweralkanoyloxy, or triloweralkylsilyloxy;
$R_{25}$ is hydrogen or halogen;
$R_{30}$ is hydrogen, halogen, hydroxy, loweralkoxy, loweralkanoyloxy, hydrazono, or semicarbazono; and
the broken line represents a single or double bond between carbons 24 and 25.

3. The compound of claim 2 wherein
$R_1$ is hydrogen or substituted benzenesulfonyl;
$R_5$ is hydrogen,
$R_{24}$ is hydrogen or loweralkoxy;
$R_{25}$ is hydrogen;
$R_{30}$ is hydrogen, halogen, hydroxy, loweralkoxy, loweralkanoyloxy, hydrozono, or semicarbazono; and
the broken line represents a single or double bond between carbons 24 and 25.

4. The compound of claim 1 wherein
X is substructure A
Y is substructure E
Z is substructure G
$R_1$ is hydrogen, loweralkyl, lower alkanoyl, or substituted benzenesulfonyl;
$R_5$ is hydrogen, halogen, amino, nitro, or loweralkanoylamino;
$R_{12}$ is hydrogen or $R_{12}$ can be oxo provided that $R_{16}$ is hydrogen;
$R_{14a}$ is hydrogen, hydroxy, lower alkoxy lower alkenyl-loweralkoxy, lower alkanylalkyloxy, lower alkanoyloxy, polyalkoxyalkoxy, phenyl, lower alkyl, trialkylsilyloxy, diphenylphosphoryloxy, or halogen;

$R_{14b}$ is hydrogen, hydroxy, lower alkyl, lower alkenyl, phenyl, phenylloweralkyl, lower alkoxy, or lower alkanoyloxy,;

$R_{16}$ is hydrogen or $R_{16}$ can be oxo provided that $R_{12}$ is hydrogen;

$R_{24}$ is hydrogen, halogen, hydroxy, loweralkoxy, loweralkanoyloxy, or triloweralkylsilyloxy;

$R_{26}$ is hydrogen or methyl.

5. The compound of claim 4 wherein $R_1$ is hydrogen or substituted benzenesulfonyl;

$R_5$ is hydrogen $R_{12}$ is hydrogen $R_{14a}$ is hydrogen, hydroxy, lower alkoxy, lower alkenylloweralkoxy, lower alkynylloweralkoxy, lower alkanoyloxy, polyalkoxyalkoxy, or triloweralkysilyloxy;

$R_{14b}$ is hydrogen, lower alkyl, lower alkenyl, phenyl, or phenylloweralkyl;

$R_{16}$ is hydrogen;

$R_{24}$ is hydrogen, halogen, hydroxy, loweralkoxy, loweralkanoyloxy, or triloweralkylsilyloxy;

$R_{26}$ is hydrogen or methyl.

6. The compound of claim 5 wherein $R_1$ is hydrogen;

$R_5$ is hydrogen $R_{12}$ is hydrogen $R_{14a}$ is hydroxy, lower alkoxy, lower alkenylloweralkoxy, or lower alkynylloweralkoxy;

$R_{14b}$ is hydrogen, lower alkyl, or lower alkenyl;

$R_{16}$ is hydrogen;

$R_{24}$ is hydrogen, halogen, hydroxy, or loweralkoxy;

$R_{26}$ is hydrogen or methyl.

7. The compound of claim 1 wherein

X is substructure A

Y is substructure D

Z is substructure G $R_1$ is hydrogen, lower alkanoyl, or substituted benzenesulfonyl;

$R_5$ is is hydrogen, halogen, amino, nitro, or loweralkanoylamino;

$R_{12}$ is hydrogen;

$R_{14a}$ is hydrogen, hydroxy, lower alkoxy, lower alkenylloweralkoxy, lower alkynylloweralkoxy, lower alkanoyloxy, polyalkoxyalkoxy, phenyl, lower alkyl, triloweralkylsilyloxy, diphenylphosphoryloxy, or halogen;

$R_{14b}$ is hydrogen, hydroxy, lower alkyl, lower alkenyl, phenyl, phenylloweralkyl, lower alkoxy, or lower alkanoyloxy,;

$R_{16}$ is hydrogen or $R_{16}$ can be oxo provided that $R_{12}$ is hydrogen;

$R_{24}$ is hydrogen or loweralkoxy,;

$R_{25}$ is hydrogen; and the broken line represents a single or double bond between carbons 24 and 25.

8. The compound of claim 7 wherein $R_1$ is hydrogen, or substituted benzenesulfonyl;

$R_5$ is hydrogen;

$R_{12}$ is hydrogen;

$R_{14a}$ is hydrogen, hydroxy, lower alkoxy, loweralkenylloweralkoxy, lower alkynylloweralkoxy, polyalkoxyalkoxy, triloweralkylsilyloxy, or halogen;

$R_{14b}$ is hydrogen, lower alkyl, lower alkenyl, or phenylloweralkyl;

$R_{16}$ is hydrogen;

$R_{24}$ is hydrogen or loweralkoxy,;

$R_{25}$ is hydrogen; and the broken line represents a single or double bond between carbons 24 and 25.

9. The compound of claim 8 wherein $R_1$ is hydrogen;

$R_5$ is hydrogen;

$R_{12}$ is hydrogen;

$R_{14a}$ is lower alkoxy, lower alkenylloweralkoxy, or lower alkynlalkyloxy;

$R_{14b}$ is lower alkyl or lower alkenyl;

$R_{16}$ is hydrogen;

$R_{24}$ is hydrogen;

$R_{25}$ is hydrogen; and the broken line represents a double bond between carbons 24 and 25.

10. The compound of claim 1 which is 14-O-methyl-paraherquamide.

11. The compound claim 1 which is 14-O-ethyl-paraherquamide.

12. The compound of claim 1 which is 14-O-butyl-paraherquamide.

13. The compound which is 14-O-benzyl-paraherquamide.

14. The compound of claim 1 which is 14-O-allyl-paraherquamide.

15. The compound of claim 1 which is 14-O-propargyl-paraherquamide.

16. The compound of claim 1 which is 14-O-methoxymethyl-paraherquamide.

17. The compound of claim 1 which is 14-O-methoxy-ethoxy-methyl-paraherquamide.

18. The compound of claim 1 which is 17-methyl-paraherquamide.

19. The compound of claim 1 which is 17-methylene-paraherquamide.

20. The compound of claim 1 which is 1-N-(p-toluenesulfonyl)-paraherquamide.

21. The compound of claim 1 which is 24-methoxy-24,25-dihydro-paraherquamide.

22. The compound of claim 1 which is 14-O-trimethylsilyl-paraherquamide.

23. A method for the treatment of parasitic infections in domesticated animals which comprises treating such animals with an effective amount of a compound of claim 1.

24. A method for the treatment of insect or nematode pests of plants which comprises treating said plants or the soil in which they grow with an effective amount of a compound of claim 1.

25. A composition useful for the treatment of parasitic infections in domesticated animals which is comprised of an inert carrier and a compound of claim 1.

26. A composition useful for the treatment of insect or nematode pests of plants which is comprised of an inert carrier and a compound of claim 1.

* * * * *